United States Patent
Geissler et al.

(10) Patent No.: US 7,334,520 B2
(45) Date of Patent: Feb. 26, 2008

(54) PRINTING PRESS AND DEVICE FOR THE INLINE MONITORING OF PRINTING QUALITY IN SHEET-FED OFFSET PRINTING PRESSES

(75) Inventors: Wolfgang Geissler, Bad Schönborn (DE); Loris De Vries, Buchs (CH); Peter Ehbets, Zürich (CH); Robert Lange, Netphen (DE); Frank Muth, Karlsruhe (DE); Christopher Riegel, Bruchsal (DE); Frank Schumann, Heidelberg (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 0 days.

(21) Appl. No.: 11/593,183

(22) Filed: Nov. 3, 2006

(65) Prior Publication Data
US 2007/0113748 A1    May 24, 2007

Related U.S. Application Data

(63) Continuation of application No. PCT/EP2005/04477, filed on Apr. 27, 2005.

(30) Foreign Application Priority Data
May 3, 2004    (DE) .................. 10 2004 021 600

(51) Int. Cl.
*B41F 13/24*    (2006.01)
*G06K 9/00*    (2006.01)

(52) U.S. Cl. .................. 101/232; 101/DIG. 45; 382/112; 250/559.01; 250/226; 356/430

(58) Field of Classification Search ........ 101/231–233, 101/408–410, DIG. 45; 250/227.11, 559.01, 250/226; 348/88, 128; 382/112; 271/82
See application file for complete search history.

(56) References Cited

U.S. PATENT DOCUMENTS

| | | | |
|---|---|---|---|
| 3,756,725 A | 9/1973 | Manring | 356/175 |
| 3,912,364 A * | 10/1975 | Hudson | 385/46 |
| 4,830,499 A | 5/1989 | Kohno et al. | 356/400 |
| 4,859,062 A | 8/1989 | Thurn et al. | 356/371 |
| 4,879,000 A | 11/1989 | Gausa | 162/198 |
| 5,029,527 A | 7/1991 | Jeschke et al. | 101/365 |
| 5,031,534 A | 7/1991 | Brunner | |
| 5,050,994 A | 9/1991 | Kipphan et al. | |
| 5,095,818 A | 3/1992 | Bialek | 101/183 |

(Continued)

FOREIGN PATENT DOCUMENTS

DE    2 150 319    4/1972

(Continued)

*Primary Examiner*—Daniel J. Colilla
*Assistant Examiner*—Marissa Ferugson-Samreth
(74) *Attorney, Agent, or Firm*—Laurence A. Greenberg; Werner H. Stemer; Ralph E. Locher

(57) ABSTRACT

A printing press for processing sheet printing materials includes at least one printing unit, a computer and a measuring device for monitoring printing quality during a printing process. The measuring device has a sensing device for measuring by color or spectrally to register the printing material. At least one sheet-guiding element leads the sheet printing material past the sensing device. A measuring device for monitoring printing quality during a printing process in a printing press for processing sheet printing materials, is also provided.

46 Claims, 13 Drawing Sheets

U.S. PATENT DOCUMENTS

| | | |
|---|---|---|
| 5,216,488 A | 6/1993 | Tuunanen et al. ....... 250/559.4 |
| 5,258,925 A | 11/1993 | Maier et al. |
| 5,329,852 A | 7/1994 | Bolza-Schuenemann et al. ..................... 101/232 |
| 5,724,437 A | 3/1998 | Bucher et al. .............. 382/112 |
| 6,050,192 A | 4/2000 | Kipphan et al. |
| 6,119,594 A | 9/2000 | Kipphan et al. |
| 6,192,140 B1 | 2/2001 | Reinhard et al. ............ 382/112 |
| 6,485,687 B1 | 11/2002 | Spangenberg et al. ...... 707/102 |
| 7,084,418 B2 | 8/2006 | Luxem et al. |
| 2003/0101884 A1 | 6/2003 | Loffler et al. ............. 101/350.2 |

FOREIGN PATENT DOCUMENTS

| | | | |
|---|---|---|---|
| DE | 30 15 103 A1 | 10/1981 | |
| DE | 32 20 360 A1 | 12/1981 | |
| DE | 30 37 622 A1 | 4/1982 | |
| DE | 33 26 346 A1 | 1/1984 | |
| DE | 37 13 279 A1 | 11/1988 | |
| DE | 38 30 121 A1 | 3/1990 | |
| DE | 38 30 732 A1 | 3/1990 | |
| DE | 40 05 558 A1 | 9/1991 | |
| DE | 41 35 814 A1 | 5/1992 | |
| DE | 43 21 177 A1 | 1/1995 | |
| DE | 43 21 179 A1 | 1/1995 | |
| DE | 198 11 150 A1 | 9/1999 | |
| DE | 199 39 154 A1 | 4/2001 | |
| DE | 100 23 127 A1 | 11/2001 | |
| DE | 103 03 282 A1 | 8/2003 | |
| DE | 102 39 973 A1 | 3/2004 | |
| JP | 61292544 | * | 12/1986 |
| JP | 04120865 | * | 4/1992 |

* cited by examiner

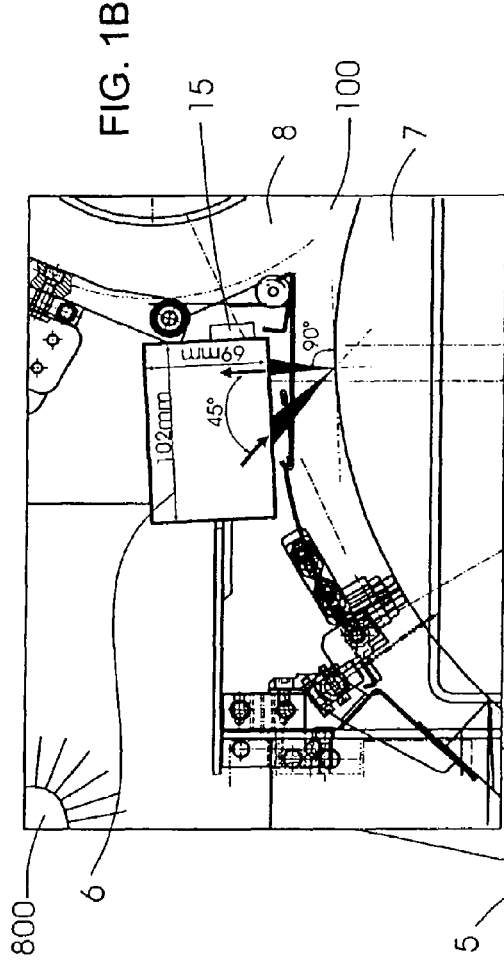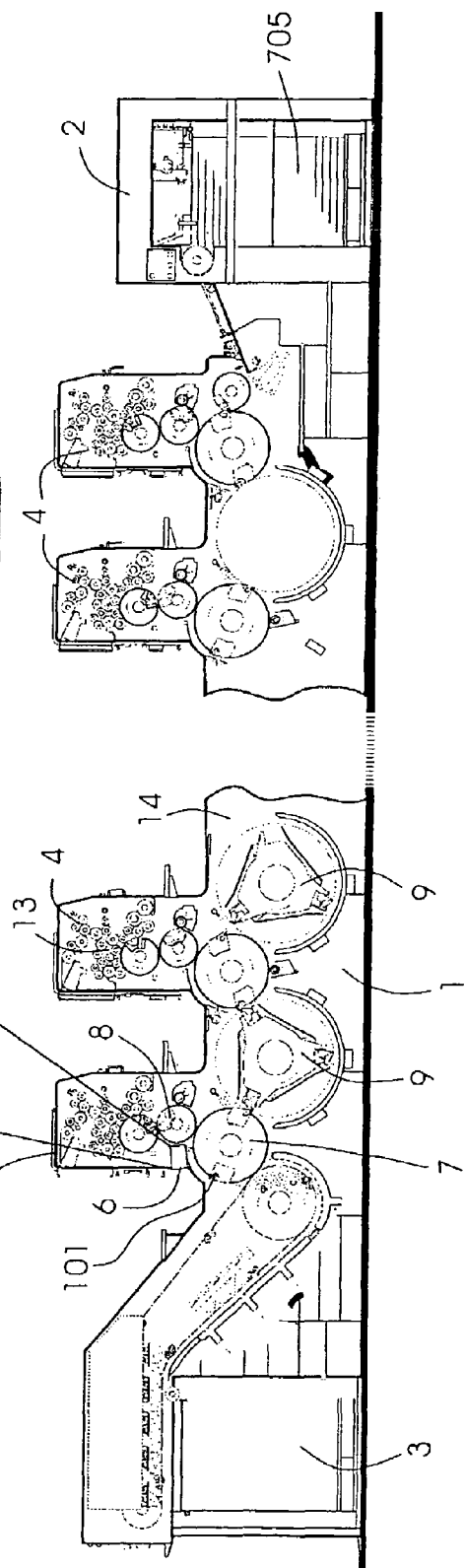

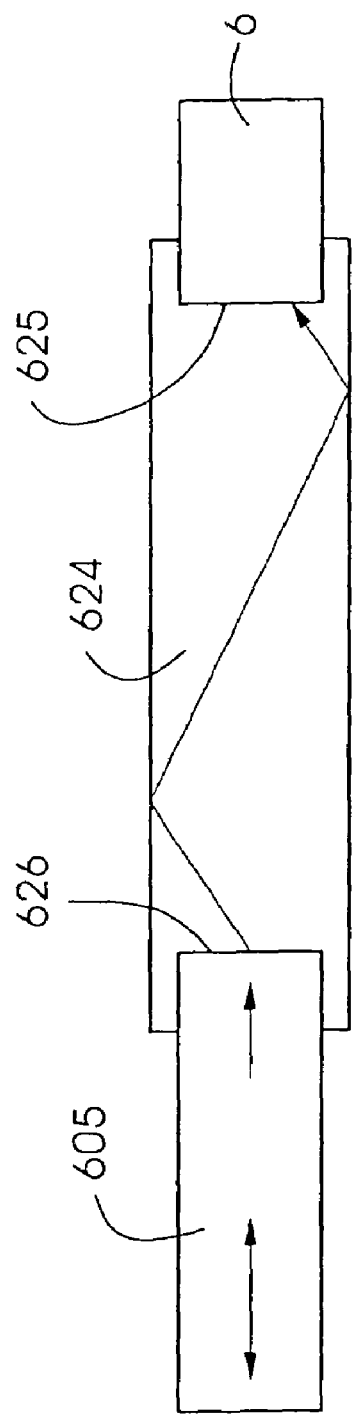
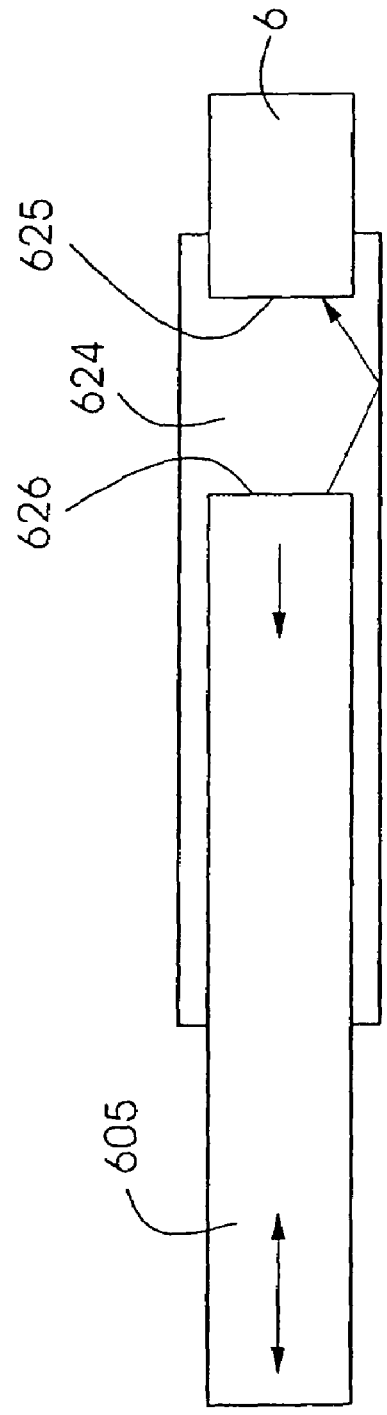
FIG. 7A
FIG. 7B

PRINTING PRESS AND DEVICE FOR THE INLINE MONITORING OF PRINTING QUALITY IN SHEET-FED OFFSET PRINTING PRESSES

CROSS-REFERENCE TO RELATED APPLICATIONS

This is a continuing application, under 35 U.S.C. § 120, of copending International Application No. PCT/EP2005/004477, filed Apr. 27, 2005, which designated the United States; this application also claims the priority, under 35 U.S.C. § 119, of German Patent Application DE 10 2004 021 600.2, filed May 3, 2004; the prior applications are herewith incorporated by reference in their entirety.

BACKGROUND OF THE INVENTION

Field of the Invention

The present invention relates to a printing press for processing sheet printing material, including at least one printing unit, a computer and a device for monitoring printing quality during a printing process. The monitoring device has a sensing device registering or recording the printing material. The invention also relates to a device for the monitoring of printing quality in sheet-fed offset printing presses.

During every printing operation, an attempt is made to achieve a situation in which printed copies correspond as far as possible to an original print. To that end, complicated quality control and monitoring of the printed printing materials by printing personnel is required in a printshop operation. According to the prior art, that is carried out through the use of visual assessment by the operating personnel and by the employment of optical measuring instruments, which measure either densitometrically or spectrally. For that purpose, in the case of sheet-fed offset printing presses, a sheet has to be removed from the delivery and is usually placed on a sheet supporting desk. The sheet is illuminated on the desk with a standardized source of illumination and is measured with the aid of optical measurement technology or assessed visually. However, that process takes time and, in addition, is made more difficult by the fact that the printing press continues to print during the quality control and, under certain circumstances, rejects arise if the assessed sheet does not correspond to expectations. Since, after each interruption to the printing process, the printing press needs a certain number of sheets until the printing process has reached a stable state again, rejects also cannot be simply prevented by shutting down the printing press quickly during the printing material inspection. Furthermore, printing personnel who are needed in order to assess the printing sheet during the quality control, are not available for other activities. Since many possible adjustments have to be made during the setup phase of a printing press, in particular in the inking unit area, rejects of between 150 and 400 sheets normally occur. That is made even more difficult by the fact that the printing process can generally only be reproduced with difficulty, since the printing result depends on a great many parameters such as ink, temperature, water, paper, printing speed, rubber blanket, condition of the printing plate, etc. All of those parameters normally change in some way from print job to print job, and it is therefore not sufficient to store the setting of a print job and to retrieve it in the same way for repeat jobs since, for example, air temperature or atmospheric humidity could have changed in the meantime, so even for the same print job, new settings have to be made due to changed environmental conditions. In that case too, a correction to the inking unit settings is necessary, which is to be automated.

Since, in the case of web-fed offset printing presses, printed newspaper webs cannot simply be removed from the machine, there are already measuring systems which attempt to measure the quality of a printed web spectrally or densitometrically. A method for operating a sensing device for optical density measurement is disclosed by German Published, Non-Prosecuted Patent Application DE 100 23 127 A1. In that case, the printed web which leaves the last printing unit in a web-fed offset printing press is guided over a deflection roll, and a sensing device for optical density measurement, color measurement or spectral measurement is disposed parallel to the deflection roll. The quality of the printed web can be determined in that way. In the description of the exemplary embodiments, it is indicated that the method disclosed in that application can also be applied during printing on sheet printing materials. However, an accurate description of how that is actually to be done cannot be gathered from that application. In particular the problem that, in the case of sheet printing materials, the guidance of the sheet printing materials over a deflection roll as in German Published, Non-Prosecuted Patent Application DE 100 23 127 A1 is not possible at all, is not solved, since sheet printing materials have to be held at least at one point by a holding device such as grippers or the press nip of the printing unit. For that reason, the device disclosed in German Published, Non-Prosecuted Patent Application DE 100 23 127 A1 is not suitable for the quality assessment of sheet printing materials during the printing process in sheet-fed offset printing presses.

SUMMARY OF THE INVENTION

It is accordingly an object of the invention to provide a printing press and a device for the inline monitoring of printing quality in sheet-fed offset printing presses, which overcomes the hereinafore-mentioned disadvantages of the heretofore-known devices of this general type.

With the foregoing and other objects in view there is provided, in accordance with the invention, a printing press for processing sheet printing materials. The printing press comprises at least one printing unit, a computer and a measuring device for monitoring printing quality during a printing process. The measuring device has a sensing device for measuring by color or spectrally to register the printing material. At least one sheet-guiding element leads the sheet printing material past the sensing device.

The present invention is distinguished firstly by the fact that the sheet printing material can be guided past the sensing device in a defined manner by at least one sheet-guiding element. Through the use of the sheet-guiding element, the sheet printing material is fixed and only then can be measured reliably by the sensing device. Suitable sheet-guiding elements are grippers of sheet guiding cylinders of a printing press or the nip between two sheet guiding cylinders. Thus, the sensing device for the quality control of the printing material can be fitted close to the press nip of a printing unit. Registering the printing quality in sheet printing materials close to the press nip offers the advantage that the sheet is guided there at its leading edge by grippers of the impression cylinder and the press nip of the printing unit. In this case, the sheet is stretched over the surface of the cylinder and thus has a defined position with respect to the sensing device. This guidance is of the utmost importance during the quality control of sheet printing materials since, as opposed to web printing materials, sheets cannot be guided over deflection rolls but have to be guided, at least on one side, by a gripper device or the press nip. The closer the sensing device is disposed to the press nip, the less the risk that the printing material will execute fluttering movements during the measurement and thus falsify the measured results. Another suitable sheet-guiding element is a sheet guiding cylinder having blower/vacuum nozzles since, there too, the sheet is guided adequately through the use of the air and in this way fluttering movements are reduced to a minimum. The sensing device can therefore in principle be incorporated at any location of a sheet-fed printing press at which the sheet is guided in any way.

In accordance with another feature of the invention, provision is made for the sensing device to measure by color, densitometrically or spectrally. Measurement by color means that measured values are registered and, for example, are displayed in the XYZ, RGB or Lab color space. This measurement by color is often also designated calorimetric measurement. Spectral measurement offers the advantage that even special colors and halftone printed areas can be measured unambiguously and readjusted appropriately. Through the use of one or more spectrometers in the sensing device, it is possible as a result to measure the values of one or more color zones one after another or simultaneously and to send these values to the computing unit of the printing press, so that the computer can compare these actual values with corresponding desired values and, if appropriate, can correct settings in the printing press.

In accordance with a further feature of the invention, provision is made for the printing material to be held in the printing unit during the sensing operation by a transport gripper of a sheet guiding drum and the press nip of the printing unit. In order not to falsify the measured results during the printing quality control, the printing material must move as little as possible since, in particular, the distance between printing material and sensing device should if possible not vary during the measuring operation. As a sheet leaves the press nip of a printing unit of a sheet-fed rotary printing press, the sheet is guided at its rear end by the press nip and is held at its front end by a sheet gripper of a sheet guiding transport drum. In this position, the printed sheet is thus held on two opposite sides and stabilized well, so that it can be measured reliably by the sensing device.

In accordance with an added feature of the invention, provision can be made for there to be a compensation device connected to the computer, which compensates for the influence of light falling on the printing material. In order to obtain a meaningful measurement, the illumination of the printing material plays an important part. In the event of changed illumination of the printing material, changed measured values arise with the same printing material, which prevents good reproducibility of the measuring operation. It is therefore necessary to create an environment which ensures this reproducibility. For this reason, the incidence of varying light on the printing material during the measuring operation should be prevented. This can be done by the measuring device and measured sheet being shielded off from the inward scattering of external light during the measuring operation. However, it may be that there are light sources present in the printing press itself which fluctuate, as viewed over time. This can be, for example, the lamp of a connected UV dryer, which shines into the last printing unit of a sheet-fed rotary printing press and could impair a sensing device installed there. In this case, the influence of such an external light source can be registered by a sensor, which measures the external light source and sends corresponding values to the computer of the printing press. The latter then compensates for the measured values determined by the sensing device through the use of the external light values registered by the sensor, in order to compute out the effect of external light in this way.

In accordance with an additional feature of the invention, it has proven to be advantageous for the sensing device to also be suitable for register measurement, position detection of register marks and print control strips as well as for determining the type of printing material. In particular, the position detection of register marks, as well as the position determination of print control strips during the color measurement is an important detail, since register measurement and color measurement function reliably only when the position of the register marks or the print control strip is firstly detected reliably. For this reason, the sensing device should contain at least one sensor for registering the position of register marks and/or print control strips, in order then to be able to evaluate the pattern of such a mark present on the printing material for the purpose of measurement. In addition, there can be a gloss sensor for registering the quality of the surface of the printing material, since the condition of the surface is also an important parameter for the control of the printing process, which should be known during the adjustment. All of these sensors can be built up individually, but can also be constructed in any desired combination as a single combination sensor or a plurality of combination sensors.

In accordance with yet another feature of the invention, as a supplement to the aforementioned embodiments, provision can be made for the sensing device to be incorporated in or after the last printing unit of the printing press, as seen in the printing material transport direction. This installation location offers the great advantage that, in the last printing unit, all of the colors have already been applied to the printing material, and therefore the overall quality of the printing material can be registered. Since the overall quality of the printing material is ultimately critical, because only it can be compared reliably with the printing original, the installation location of the sensing device in or after the last printing unit proves to be particularly advantageous.

In accordance with yet a further feature of the invention, it also proves to be advantageous for the printing press to have a sheet turning device, for at least one sensing device to be disposed before the sheet turning device and for a sensing device to be disposed after the sheet turning device. In the case of sheet-fed printing presses having perfecting equipment, the sheet is turned at least once during the printing operation, so that in that case both sides of a printing material have to be assessed for the purpose of quality control. For this reason, it is expedient, in a sheet-fed printing press having perfecting equipment, to fit one sensing device before the sheet turning device and a further sensing device after the sheet turning device. In order to be able to register the overall quality of the printing material in this case too, the first sensing device should be fitted between the last printing unit before the turning and the sheet turning device itself, and a second sensing device should be fitted in or after the last printing unit of the machine. This ensures that, both on the front and on the rear of the printing material, the state in which all of the colors or varnishes or other coatings have been applied to the respective side of the printing material, is registered.

In accordance with yet an added feature of the invention, provision is expediently made for the sensing device to have the form of a measuring beam. When a sensing device is used in sheet-fed rotary printing presses close to the press nip, the result is primarily a space problem. For this reason, the sensing device must take up as little space as possible, which can be achieved by the formation as a measuring beam which extends over the entire width of a printing material. Thus, the measuring beam extends parallel to the axes of the impression cylinder and transport cylinder and, due to its low cross section, can be mounted immediately by the press nip of the printing unit. The cross section of the measuring beam should therefore be as small as possible or its shape should be matched to the space, for example by the cross section tapering toward the press nip.

In accordance with yet an additional feature of the invention, provision is made for the measuring beam to be mounted in such a way that it can be displaced in its longitudinal direction. It is usual for a plurality of inking zones to be distributed over the entire width of the printing material, with in principal each inking zone having to be evaluated for reliable quality control. If it is not desired to install a separate sensor in the measuring beam for registration of each inking zone, it is necessary to make the measuring beam displaceable in its longitudinal direction. As a result, the sensors can be displaced from one inking zone to another, so that all of the inking zones over the entire width of a printing material can also be registered with relatively few measuring sensors. Since the measurement should proceed automatically, the measuring beam has a drive motor, which drives the same displaceably in its longitudinal direction.

In accordance with again another feature of the invention, the sensing device is rotatably mounted and/or replaceable and is suitable for use in further printing units. Since the sensing device is disposed close to the press nip, there is a high risk of contamination, because the inks and varnishes applied to the printing material are still wet after leaving the press nip and, consequently, can leave traces behind on a sensing device installed close to the press nip. In order to be able to clean the sensing device simply, this should either be reasonably easily removable or at least rotatably mounted, so that the maintenance personnel or the printer can easily make access to the side of the sensing device facing the printing material. If the sensing device is removable, for example in the case of a sheet-fed rotary printing press for perfecting which has two sensing devices, it can additionally be replaced by another sensing device. In this way it is possible for example to check whether the sensing devices are still functioning correctly or whether a sensing device has a defect. In addition, the measuring beam can be transferred into upstream printing units, if the intention is to print with fewer colors or the installation location is changed for other applications, such as a replaceable varnishing unit in the last printing unit.

In accordance with again a further feature of the invention, it has proven to be particularly advantageous in practice for the measuring beam to have the form of a U profile open in the direction of the printing material and to accommodate at least one movable measuring carriage in the interior of the U profile. Given such a construction of the measuring beam, the measuring beam itself does not have to be constructed to be displaceable. Instead, the displacement movement over the entire width of the printing material is carried out by the movable carriage located in the measuring beam. To this end, the carriage is driven by a motor, preferably a linear electric motor, which permits precise and rapid movement of the carriage in the measuring beam. During the measurement, the motor can drive the carriage continuously or in stepping operation. In stepping operation, the carriage is at a standstill during the measurement, while in continuous operation the carriage also moves during the measuring operation. It is also possible for there to be a plurality of measuring carriages in the measuring beam, each of which carries one or more measuring heads. Each carriage is then driven by an individual motor, so that the carriages can be moved independently of one another. The U profile likewise imparts stability and rigidity to the measuring beam, which improves the accuracy when registering the measured values on the printing material surface. In addition, the U profile simultaneously protects the carriage on three sides against environmental influences from outside.

In accordance with again an added feature of the invention, provision is made for the measuring beam to have at least one removable side wall. For maintenance purposes, it is necessary under some circumstances to be able to remove the carriage from the measuring beam in order to obtain access to individual parts of the carriage. For this purpose, the measuring beam has a removable end wall at least at one end, so that the carriage can be removed laterally out of the measuring beam without difficulty. For this purpose, the end wall is equipped in such a way that it can be removed easily, for example through the use of a screw connection, plug-in connection or clamp connections.

In accordance with again an additional feature of the invention, the carriage has one or more measuring modules. As in the case of the longitudinally displaceable measuring beam, it is not necessary either for there to be a measuring head or measuring modules in the movable carriage for each inking zone of the printing material to be measured. Instead, it is sufficient for it to be possible to move successively to all of the inking zones over the entire width of the printing material by using the measuring heads present in the carriage.

In accordance with still another feature of the invention, in an expanded refinement, thought is given to the measuring carriage having one or more register sensors. In addition to the measuring modules for the spectral, densitometric or color measurement of the printing material surface, register sensors can additionally be accommodated in the carriage and, on one hand, are firstly able to register the position of a register mark on the printing material and, on the other hand, are able to appropriately evaluate the register marks themselves, in order to be able to correct register errors in this way. Since the register sensors are accommodated in the movable carriage, it is possible, through the use of lateral movements of the carriage, to position the register sensors appropriately as well and therefore to align them with the register marks present on the printing material.

In accordance with still a further feature of the invention, advantageously, the measuring carriage has at least one illuminating device. In addition to the problems with external light sources, it is necessary for reliable measurement that the printed material be illuminated with a standardized source of illumination. The standardization ensures that each printing material is evaluated under the same illumination conditions during each measurement. In order to ensure these standardized conditions, it is necessary that in addition, during each measurement, the measuring heads and the illuminating device have the same configuration. It is therefore advantageous if both the illuminating device and the measuring heads are accommodated in the carriage, since then the illuminating device and the measuring heads are not configured in such a way that they can move relative to each other, and thus there are always constant geometric conditions present. Measuring heads and illuminating devices can be combined into one measuring module, and it is possible for the light source itself to be located outside the measuring module. The light source is preferably constructed as a flash lamp, which illuminates the printing material precisely at the measuring times. Therefore, as in the case of a stroboscope, the movement of the printed sheet with respect to the measuring module can be frozen, and at the same time the measuring location is illuminated with high intensity. The triggering of the flash lamp is synchronized with the movement of the measured sheet through the control computer of the printing press, or an additional detection mark is applied at a defined distance from the print control strip, which is sensed by a sensor and then triggers the flash lamp. Since the power of a lamp decreases as seen over the entire lifetime, it is expedient to dimension the lamp in such a way that, at the start, it has to operate only with a reduced output, for example with 50% of its maximum output, in order to generate sufficient light. With increasing aging, the output of the lamp is controlled up to the maximum, so that the light output remains constant as seen over the entire lifetime.

In accordance with still an added feature of the invention, it is also advantageous for the sensing device in a sheet-fed rotary printing press to be configured as a sheet-guiding element at the same time. Since in sheet-fed rotary printing presses, as opposed to web-fed rotary printing presses, each sheet has to be guided individually, sheet guide plates and suction/blown air nozzles for sheet guidance are fitted at many points in the sheet transport path of a sheet-fed rotary printing press and, in addition to the sheet grippers and guides in the press nip, permit secure and reliable transport through the printing path. Since the sensing device is fitted very close to the sheet surface, there is always the risk that the sheet can come into contact with the sensing device. For this reason, the sensing device can simultaneously be formed as a sheet guide plate, since the distance between printing material and sensing device can then be monitored more simply. For example, further suction or blown air nozzles can also be integrated in the sensing device transversely with respect to the sheet transport direction. The distance of the printing material from the sensing device can be controlled with such nozzles. In any case, accurate sheet guidance in the region of the sensing device is of great importance for exact measured results and therefore reliable quality control of the sheets.

In accordance with still an additional feature of the invention, through the use of the sensing device, the position of a print control strip can be detected and the measurement time for color measurement can be registered. The inking zones of a printing material are evaluated by using a print control strip which is printed on the printing material transversely or longitudinally with respect to the sheet transport direction, is likewise inked during the printing operation and thus permits quality assessment of the inking of the printed material. This print control strip, in a way similar to the register mark, also has to be registered first in terms of its position before its evaluation. In addition, the measurement must be carried out exactly when the print control strip is located under the sensing device. For this purpose, the sensing device has a sensor which determines the position of the print control strip and simultaneously sends a trigger signal to the evaluation electronics of the sensing device when the print control strip is present and ready for measurement. The position of the print control strip as well as that of a register mark can be configured in such a way that they can be registered more easily by an appropriately encoded position measuring area being applied before the print control strip and the register mark, containing information about the position of the print control strip or the register mark and being registered by a sensor of the sensing device. Then, in the start-up phase of the printing operation, the sensing device can be brought into an appropriate position in good time through the use of motor adjustment in order to be able to detect the print control strip or the register mark reliably, if there are deviations. However, it is normally sufficient to evaluate the position measuring area during the start of printing and subsequently at greater intervals, since the position of the print control strip with respect to the sensing device should no longer change during continuous printing. In this case, therefore, only one control is applied.

In accordance with another feature of the invention, for a fully automatic inline, real-time or closed-loop measuring system, it is imperative that the sensing device be capable of connection to a computer. In this way, the data from the measuring heads and further sensors can-be transmitted directly to the computer of the printing press, which is able to process this data during the control of the printing press. In addition, it is possible to dispense with an individual computer in the sensing device itself, which saves overall size and in this way permits a correspondingly small sensing device. If there is nevertheless sufficient space in the sensing device, there can of course also be a computing device present in the latter.

In accordance with a further feature of the invention, in order to increase the accuracy of the measuring results, provision is made for the sensing device to have one or more measuring modules and for it to be possible for calibration data for each measuring module to be stored in the computer. The measuring heads in the measuring modules have to be re-calibrated from time to time in order to permit a sufficiently accurate measurement. The data determined during the calibration operation is then stored in a computer for following measurements, with it being possible for this to be the computer of the printing press or a computer having a storage device in the sensing device itself.

In accordance with an added feature of the invention, the sensing device has an Ethernet interface or another standardized computer interface. If standardized computer interfaces are used, it is possible to fall back on the architecture of commercially available computers, and access can also be made to all of the possibilities of such standardized computer interfaces. In particular, program updates can be transmitted and the sensing device can be connected directly to the interfaces of a PC or laptop, which is not possible in the case of proprietary interfaces without an adapter. Furthermore, the protocols used in standardized computer interfaces can be used for secure data transmission without new development being required specifically for this purpose.

In accordance with an additional feature of the invention, it is also possible for the illuminating device to be provided with optical waveguides, which are assigned to individual measuring modules at one end and, at the other end, are assigned to at least one light source in a thoroughly mixed bundle. Since there is little space in the sensing device and in particular in the embodiment having a measuring carriage which is located in the interior of the measuring beam, a separate light source cannot be used for each measuring module. Through the use of optical waveguides, however, it is possible to supply the light from one light source or a plurality of light sources to a plurality of measuring modules. The optical waveguides at the end facing the light source or the light sources are advantageously thoroughly mixed in order to ensure a uniform distribution of the light to all of the optical waveguides. The optical waveguides can, for example, be flexible glass fibers, which can be matched without difficultly to the limited space in the sensing device. Since these optical waveguides are very low-loss, they are very well suited to the illumination of the measured regions for the measuring heads. The restriction to one light source is also beneficial for thermal reasons, since otherwise the interior of the measuring beam is heated up highly and appropriate cooling devices then have to be provided.

In accordance with yet another feature of the invention, in order to improve the measurement accuracy, provision is additionally made for there to be one or more temperature sensors in the sensing device. Through the use of such temperature sensors, firstly the current measuring conditions can be registered accurately and, secondly, the thermal health of the system can be monitored. For example, the measurements can be interrupted or the sensing device can be switched off, if a temperature is measured which is located outside a permissible range. In this case, an alarm signal can additionally be displayed to the operating personnel of the printing press, in order to request the former to check the sensing device. In addition to temperature sensors, there can also be humidity sensors in the sensing device, with which the atmospheric humidity in the printing unit can be registered. However, a rise in temperature can also be determined through the use of register sensors on the measuring beam. If the measuring beam expands as a result of temperature, then the distance between the register sensors also changes, in particular the sensors in each case placed at the outer end of the beam. Since the spacing of the register marks on the sheet does not change, however, the register sensors on the measuring carriage must be moved to a different location in order to register the marks. This location change is registered and evaluated by the measuring electronics, which means that the longitudinal expansion of the measuring beam can be calculated. The temperature can be determined therefrom through the thermal expansion coefficient of the beam material.

In accordance with yet a further feature of the invention, a plurality of configurations of electronics is also provided for processing the signals of the measuring heads, which in each case provide different advantages. For example, on one hand the electronics for processing the signals of the measuring heads can be accommodated outside the measuring beam. In this case, the electronics are protected against thermal loading by the light sources in the interior of the measuring beam and the space required in the measuring beam is reduced, since the electronics are located outside. Of course, the electronics for processing the signals of the measuring heads can also be located inside the measuring beam. Although this requires more space within the measuring beam, the transport of the measured data from the sensing device to the computer of the printing press for this purpose is made easier, since the signals of the measuring heads can already be conditioned within the measuring beam into a data format suitable for the transmission to the computer.

In accordance with yet an added feature of the invention, there are also a number of possibilities for the configuration of the light source. If the light source is located outside the measuring beam, then this configuration also reduces the overall size of the measuring beam. In addition, heating of the measuring beam by the light source is avoided. Furthermore, the light source can also be located in the interior of the measuring beam but outside the measuring carriage of the measuring beam. Since the sensitive measuring heads are located on the carriage, they can be protected against the thermal radiation from the light source in this way. Nevertheless, however, it is also possible to place the light source in the carriage of the measuring beam. The great advantage in this case is that the light source is moved together with the carriage and thus no removable optical waveguides between light source and carriage are required, as is necessary in the two other cases. Since removable optical waveguides are ultimately subject to wear, the configuration with the light source in the carriage improves the lifetime of the overall system considerably. The thermal problems of the light source then have to be solved through the use of appropriate insulation of the same with respect to the measuring electronics. This requires an increased amount of space, but can be implemented with the measures currently known.

In accordance with yet an additional feature of the invention, provision is further made for the light source to be located outside the moving measuring carriage, for there to be end faces of a first bundle of optical waveguides, located and aligned parallel to one another on the movable carriage, and corresponding end faces of a second bundle of optical waveguides on the measuring beam, and for it to be possible to bridge the interspace between the two bundles of optical waveguides by optics. In addition to the possibility of coupling the light source to the movable carriage by optical waveguides affected by wear, this configuration offers the advantage that in this case it is possible to dispense with these wearing parts. In this case, the bundles of optical waveguides are located with their ends opposite one another, and it is possible for the distance between the ends of the bundles of optical waveguides to vary as a function of the position of the movable carriage. The different distance between the optical waveguides is then bridged through the use of an optical trombone, as it is known, that is to say a silvered tube. Since the carriage moves in only a relatively small range, such a configuration can be implemented without relatively great problems, and it is also possible, if required, for suitable lens optics to also be used between the bundles of optical waveguides.

In accordance with again another feature of the invention, provision is additionally made for the sensing device to be provided with a cooling device. In particular, in the configuration with a light source located in the carriage, it is necessary to cool the entire sensing device, since otherwise, firstly, the measured results will be falsified and, secondly, the temperature-sensitive measuring components of the sensing device can be affected detrimentally. Such a cooling device does not necessarily have to be accommodated in the carriage itself, but can be disposed in the measuring beam itself, for example, by the latter having a double wall in which cooling liquid can circulate. Of course, separate cooling ducts can also be fitted to the measuring beam.

In accordance with again a further feature of the invention, provision is advantageously made for the sensing device to be protected against contamination through the use of a transparent cover. Since the measuring heads of the sensing device come into contact with the printing material because of the short distance from the latter and can be smeared by the fresh printing ink, it is necessary to protect the sensing device against the latter. Through the use of a transparent cover, such protection is possible, while the measuring heads continue to have a clear view of the printing material. In order to prevent scratching of the cover, it has proven to be advantageous to produce the transparent cover from toughened or hardened glass.

In accordance with again an added feature of the invention, in order to ensure reliable functioning of the inline or real-time measuring device, it is advantageous for the sensing device to contain a device for monitoring the condition of the transparent cover. Since the transparent cover becomes smeared more and more over time as a result of contact with freshly printed printing materials, and therefore the quality of the measured results necessarily decreases, it is worth recommending a monitoring device which registers the basic contaminants and, beginning from a specific no longer admissible level of contamination, sends an alarm signal to the computer of the printing press.

In accordance with again an additional feature of the invention, provision is additionally advantageously made for the transparent cover to be replaceable. In order to avoid replacing the entire measuring beam, the transparent cover is configured in such a way that it can be replaced separately. It is possible for it to be secured to the measuring beam by a screw connection, clamp connection or plug-in connection. In this way, it is readily possible to replace the contaminated cover and to insert a clean cover, so that the cover does not have to be cleaned in the printing press.

In accordance with still another feature of the invention, provision is additionally made for the measuring modules to be provided with at least one movable mechanical shutter. This shutter does not have to be fitted directly to the measuring modules, but can be constructed in such a way that the entire sensing device with the measuring heads is closed against environmental influences. For this purpose, a shutter can be introduced underneath the measuring heads and measuring modules. The shutter thus protects the measuring heads and the entire measuring beam against contamination. This shutter is then opened only when measurements are actually carried out. In this way, contamination of the measuring beam is reduced to a minimum. In this case, it can be possible for the mechanical shutter device to be driven by one or more drives as a function of the operating state of the printing press. However, the movement of the shutter can also be triggered or effected by the movement of the measuring carriage or measuring beam itself when the latter moves into the measuring position. In addition, when it is not being used, the measuring beam can be moved into a position in which it is protected against environmental influences. For this purpose, there is a device provided which is able to move the measuring beam as a whole.

In accordance with still a further feature of the invention, provision is made for the sensing device to include a sealed housing. In order to prevent the penetration of dirt and dust, in particular fine ink particles, into the interior of the sensing device, the latter is provided with a housing which, for example, is implemented by using IP 65 technology, in order to prevent damage to the sensitive measuring sensors installed in the sensing device. If the measuring beam is configured in a U shape, it is sufficient to seal off the transparent cover of the measuring heads and lateral side walls of the measuring beam appropriately in order to protect the interior of the measuring beam against environmental influences. Instead of sealing off the measuring beam against external influences, a positive pressure generated by a small compressor can also be used, so that no dirt penetrates even if the beam has a leak or openings.

In accordance with still an added feature of the invention, if the measuring beam is open at the bottom, the measuring carriage can also be protected against dirt by air being blown into the measuring beam, flowing around the measuring carriage and leaving the beam on its open underside. Penetration of dirt particles into the interior of the beam can be prevented through the use of the air stream oriented outward on the underside of the beam. At the same time, as a sheet-guiding element, the air stream forces the printing material away from the measuring beam and in this way prevents contact between the printing material and the measuring beam.

In accordance with still an additional feature of the invention, provision is made for one or more parts of the sensing device to be provided with dirt-repellent surfaces. As already mentioned, at least the side of the sensing device that faces the printing material comes into contact with the wet surfaces of the printing material from time to time and therefore suffers contamination. If these surfaces are coated in a dirt-repellent manner, these contaminants are reduced further, even without cleaning methods. Such dirt-repellent surfaces are formed of TEFLON®, polytetrafluoroethylene (PTFE) or ORMOCER®, a hybrid polymer, for example. At the same time, the subsequent cleaning of the surfaces is made easier.

In accordance with another feature of the invention, it is additionally intended that cleaning tools be provided which are matched to the shape of the part of the sensing device to be cleaned. These cleaning tools are in particular matched to the shape of the areas to be cleaned, in order for example, to make the cleaning operation of the transparent cover easier in this way. At the same time, through the use of the specifically adapted cleaning tools, the risk that the surfaces of the sensing device will be scratched is reduced. In particular, the transparent cover must be protected against scratching, since otherwise scattered light can arise and, in addition, the measuring heads can be confused.

In accordance with a further feature of the invention, it has proven to be advantageous for webs to be disposed on the side of the transparent cover of the sensing device that faces the printing material. These webs prevent direct contact of the printing material with the transparent cover, since the printing material can come into contact only with the webs and not with the transparent cover itself. In this way, the transparent cover is reliably protected against contamination and cleaning operations are thus avoided. Since the webs in this case are necessarily located in the optical path of the measuring heads and of the illuminating device, appropriate precautions have to be taken. If the webs are located close to the optics of the measuring heads and the illuminating device, although there is a reduction in the measured intensity, this can be corrected through the use of appropriate calibration. This calibration has to be performed appropriately for each measuring position of the sensing device and then permits reliable compensation for the interference caused by the webs. Thus, at the measured points on the printing material having measured results which are influenced by the webs, measurements are carried out on paper white. Therefore, the effect of the webs can be computed out by comparing the subsequent color measurements with the measurements on paper white. In this way, the illuminating device is adapted to the webs which are present or the effect of the webs is compensated for through the use of appropriate calibration.

With the objects of the invention in view, there is concomitantly provided a measuring device for monitoring printing quality during a printing process in a printing press for processing sheet printing materials. The measuring device comprises a sensing device registering the printing materials. The sensing device measures by color or spectrally.

Other features which are considered as characteristic for the invention are set forth in the appended claims.

Although the invention is illustrated and described herein as embodied in a printing press and a device for the inline monitoring of printing quality in sheet-fed offset printing presses, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1A is a diagrammatic, side-elevational view of a sheet-fed printing press having printing units;

FIG. 1B is an enlarged, fragmentary, side-elevational view of a measuring beam in the last printing unit of the printing press of FIG. 1A;

FIG. 7A is an elevational view of an optical waveguide configuration in the measuring beam with an optical interspace;

FIG. 7B is an elevational view of the optical waveguide configuration of FIG. 7A with a reduced optical interspace;

DESCRIPTION OF THE PREFERRED EMBODIMENTS

Figure 2:
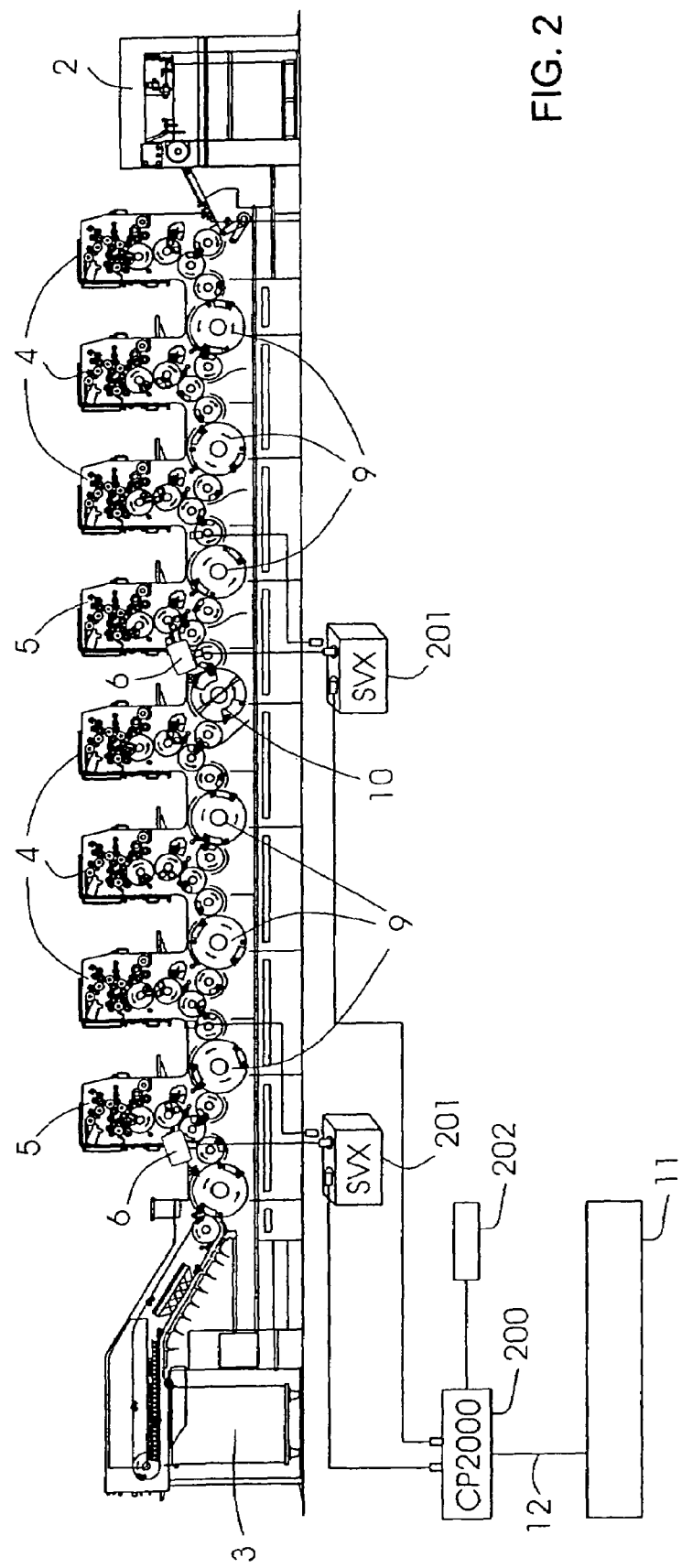
FIG. 2 is a reduced, side-elevational view of a sheet-fed printing press for perfecting.

Referring now to the figures of the drawings in detail and first, particularly, to FIG. 1A thereof, there is seen a sheet-fed rotary printing press 1 having a sheet feeder module 2 and a sheet delivery module 3 as well as four printing units 4, 5 disposed therebetween. Of course, this configuration of a sheet-fed rotary printing press 1 is to be understood only as an example, since the number of printing units 4, 5 between the sheet feeder 2 and the sheet delivery 3 plays no part in the essence of the invention. The printing units 4, 5 are connected to one another through transport cylinders 9, so that printed sheets 705 stacked in the sheet feeder 2 are conveyed through the individual printing units 4, 5 to the delivery 3 and can be printed in the printing units 4, 5. The last printing unit 5 seen in the sheet running direction differs from the other printing units 4 in that it has a measuring beam 6 as a sensing device for assessing the printing quality of printed sheets. The measuring beam 6 is therefore accommodated in the last printing unit 5, since there all of the colors applied in the printing operation are present on the printed sheets 705, and therefore the final state of the printed sheet is present. In this connection, the term printing unit 4, 5 is to be understood more widely, since of course one or more of the printing units 4, 5 can also be varnishing units, sealing units or other sheet-processing units. Even if these other units are present in the printing press 1, it is expedient for the measuring beam to be fitted in the last unit 5, in order to be able to monitor the sheet 705 with all of the varnish layers. All of the printing units 4, 5 have an impression cylinder 7 and a blanket cylinder 8, which form a press nip 100 of a printing unit 4, 5 as is indicated in FIG. 1B. Furthermore, each printing unit 4, 5 is equipped with an inking unit 13. The cylinders 7, 8 and the inking unit 13 are mounted in side walls 14 of the printing press 1 and are driven by motors and gearboxes which are present there.

The press nip 100 between the press cylinders 7, 8 can be seen more clearly in the enlargement of FIG. 1B. The enlargement of the surroundings of the press nip 100 in the last printing unit 5 together with the measuring beam 6 additionally shows the approximate size relationships of the cross section of the measuring beam 6 as compared with the diameter of the press cylinders 7, 8. Sheet grippers 101, which are also fitted to the impression cylinder 7, guide the sheet 705 around the impression cylinder 7, accept it from the transport cylinder 9 and transfer it to the delivery 3. During the measuring operation using the measuring beam 6, the printed sheet 705 is held firstly at its rear end by the press nip 100 and secondly at its leading end by the sheet gripper 101. This ensures that the sheet 705 can only minimally move during the measuring operation, which is of importance to the measuring operation in as much as the distance between the sheet 705 and the measuring beam 6 should if possible not vary during the measurement. The dimensions of the cross section of the measuring beam 6 shown in FIG. 1 in the case of a printing press 1 with a 102 cm sheet format are 102 mm in width and 69 mm in height at its end face. Furthermore, the measuring beam 6 is inclined slightly with respect to the horizontal, so that it runs parallel to the surface of a sheet 705 when the latter is being guided by the sheet gripper 101 and the press nip 100.

A sensor 15 is fixed to the measuring beam 6, but it can also be integrated into the measuring beam 6. This sensor 15 is an optical sensor, for example a camera, which is able to detect markings on the printed sheet 705. In addition, the sensor 15 can be used for the purpose of observing external light sources 800 and triggering the measuring operation of the measuring beam 6. To this end, the sensor 15 is linked to measuring electronics 201 and a computer 200 of the printing press 1, seen in FIG. 2. Thus, the measuring operation can be controlled by the sensor 15 in such a way that measurements are made only when no external light 800 is falling on the measuring area or directly into the sensing device 6. The sensor 15 can include a combined sensor or a plurality of separate sensors. It is also possible for a plurality of sensors 15 distributed over the entire length of the measuring beam 6 to be provided. The sensors 15 can also be integrated into the measuring beam 6.

FIG. 2 shows a sheet-fed rotary printing press 1 which, as distinct from FIG. 1, is equipped with a sheet turning device 10 so that, in the event of perfecting, one side of a sheet 705 can be printed in the first four printing units 4, 5 and the other side can be printed in the second four printing units 4, 5. For this reason, the printing press 1 in FIG. 2 has two printing units 5 to which measuring beams 6 are fitted, since both the front and the rear sides of a sheet must be monitored in each case by a measuring beam 6. In order to be able to assess the final state of a printed sheet 705 both in relation to the front and to the rear in this case as well, the measuring beams 6 are located in the last printing unit 5 before the turning device 10 and in the last printing unit 5 before the sheet delivery 3. As a special feature, the sheet-fed printing press 1 in FIG. 2 has the possibility of displacing the measuring beam 6. This means that the measuring beam 6 is configured in such a way that it can be removed easily and can also be installed in another printing unit 4. For this purpose, connections are also fitted to the printing units 4 preceding the two printing units 5 in FIG. 2. The printing units 5, 4 constructed to accommodate a measuring beam 6 are provided with electrical connections for this purpose, which are in each case connected to measuring electronics 201. When the measuring beam 6 is plugged into the respective printing unit 5, 4, the measuring electronics 201 is automatically notified through appropriate encoding as to the printing unit 5, 4 in which the measuring beam 6 is currently located. The measuring electronics 201 are in turn connected to a control desk and the computer 200 of the printing press 1, so that all of the measured values can be displayed there to the operating personnel of the printing press 1. In addition, the settings of the printing press 1 can be changed on the operating desk in order to control the printing quality. The computer 200 of the printing press 1 is additionally connected to prepress devices 11 over a cable-bound or wireless connection 12, for example over an Internet connection as well. Such devices 11 are in particular plate exposers for producing printing plates for offset printing presses. As a result of the connection 12 to the prepress stage 11, it is possible to use data originating from the measurements of the measuring beam 6 for changing the production process in the prepress stage 11 as well. Therefore, further-reaching changes in the printing process can be made than would be possible through the use of simple changes to the settings of the printing press 1. In addition, the production of the printing plates can be optimized. It is also possible for a hand-held measuring instrument 202, which can be used for the purpose of calibrating measuring modules 603, seen in FIG. 3, to be connected to the computer 200 of the printing press 1.

Figure 3:
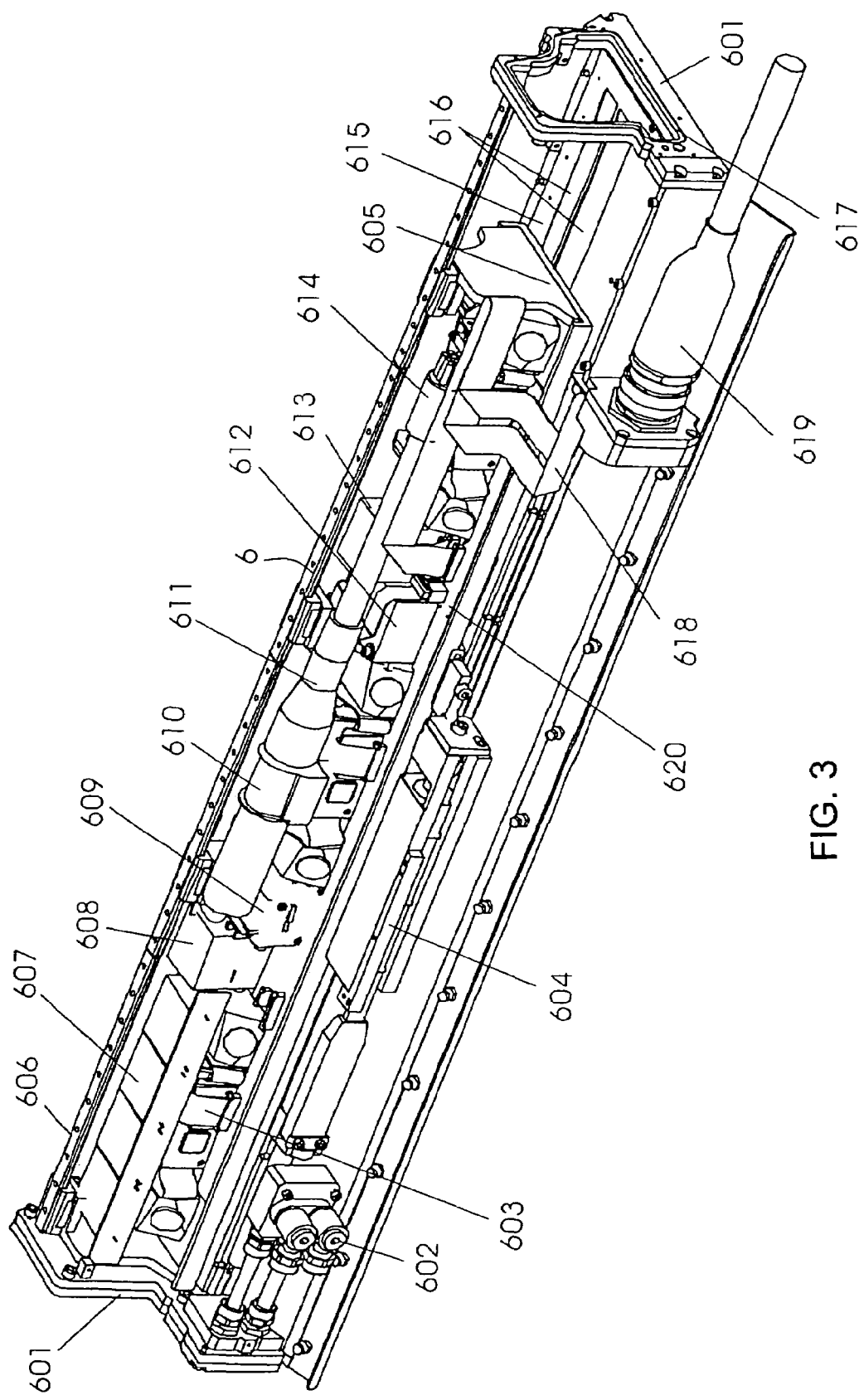
FIG. 3 is an enlarged, perspective view of an internal region of the measuring beam.

The interior of the measuring beam 6 is depicted in FIG. 3. The measuring beam 6 is constructed in such a way that it can be fixed in the printing unit 5, 4, while a movable measuring carriage 605 is disposed in the interior of the measuring beam 6. The measuring beam 6 extends over the entire width of a printed sheet, in order to be able to reliably monitor the edge regions of the printed sheet. The measuring carriage 605 can be moved in the interior of the measuring beam 6 for this purpose, in order to likewise be able to measure over the entire width of the sheet. In order to register or record the surface of the printed sheet, the measuring carriage 605 in FIG. 3 has eight measuring modules 603 having eight measuring heads 622 seen in FIG. 5. It is possible for the measuring carriage 605 to be moved in a plurality of steps or continuously so that, in the case of 4 colors, after 16 measurements, all 32 inking zones of a plurality of printed sheets 705 have been measured. In order to carry out this movement operation, the measuring carriage 605 is mounted in a guide rail 606, being driven by a linear motor 604. The measuring carriage 605 can be removed laterally from the measuring beam 6 by removing side walls 601, for the purpose of simple maintenance of the measuring carriage 605. For this purpose, the side walls 601 are configured so as to be easily removable, that is to say they are fixed to the housing of the measuring beam 6 by a plurality of screws.

The measuring beam 6 substantially includes a U profile which is open on the side facing the printed sheet. In order to prevent the penetration of dirt and, in particular, printing ink, the open side of the U profile is closed by a removable base 615, which additionally has transparent parts 616 made of glass, so that the measuring modules 603 on the measuring carriage 605 are able to sense the printing material located underneath through the base 616 of the measuring carriage 605. There is further equipment on the measuring carriage 605, besides the measuring modules 603, together with their electronics. Since the measuring modules 603 also have illumination modules 623 seen in FIG. 5 in addition to the spectral measuring heads 622, the measuring carriage 605 must be provided with a source of illumination 610. The source of illumination constitutes a flash lamp 610, which is supplied with electrical power by a mains power unit 612 located on the measuring carriage. The mains power unit 612 in turn and electronics of the measuring modules 603 are connected to the housing of the measuring beam 6 by flexible electric cables 618. The end of the flexible electric cable 618 fixed to the housing of the measuring beam 6 ends in an electric plug connector 619, through the use of which the measuring beam 6 is connected to the electrical power supply of the printing press 1 and the measuring electronics 201. In this case, the connection of electrical power and signal transmission can be carried out through the use of a plug-in or rotatable combination plug. All of the electrical components, including the measuring modules 603, are fitted on one or several circuit boards 631, in order to ensure short current and signal paths in a small space.

Since there is only one flash lamp 610 on the measuring carriage 605, its flash light must be transported to the individual illuminating modules 623 through the use of injection optics 611 and following optical waveguides 614. In addition to the mains power unit 612 of the flash lamp 610, there are also flash capacitors 607 on the measuring carriage 605 in order to provide the necessary energy. In addition, the measuring carriage 605 contains a distributor device 620 for distributing electric energy to the individual electrical loads and for distributing the electric signals of the components networked with one another in the measuring carriage 605. However, the sensing device 6 is not only capable of measuring the surface of a printed sheet spectrally, but it is also used for registering or recording register marks and for evaluating the same. To this end, the measuring carriage 605 has a right-hand register sensor 608 and a left-hand register sensor 613. It is therefore possible to register or record the register marks in the edge regions of a printed sheet. There can also be further register sensors, for example each measuring module 603 can include a register sensor, in order to ensure that a plurality of register marks over the entire width of the printing material 705 can be measured.

Since all of the electronics in the measuring carriage 605 are accommodated into a very small space, for example 70 percent of the volume of the measuring carriage 605 is filled with components, a great deal of waste heat is produced in a relatively small space. In order to be able to carry away the waste heat and in particular to prevent damage to and influence on the measuring modules 603, the interior of the measuring beam 6 is liquid-cooled. A closed cooling circuit is produced by a plurality of ducts 621 shown in FIG. 4 in the interior of the measuring beam 6 and side walls 601. The cooling circuit is closed by coolant ducts 617 in the side walls 601. The coolant ducts 621, 617 are supplied with coolant through a coolant connection 602 on the outside of the measuring beam 6. A pump for circulating the coolant therefore does not have to be fitted in the interior of the measuring beam 6 itself, but can be connected externally.

Figure 4:
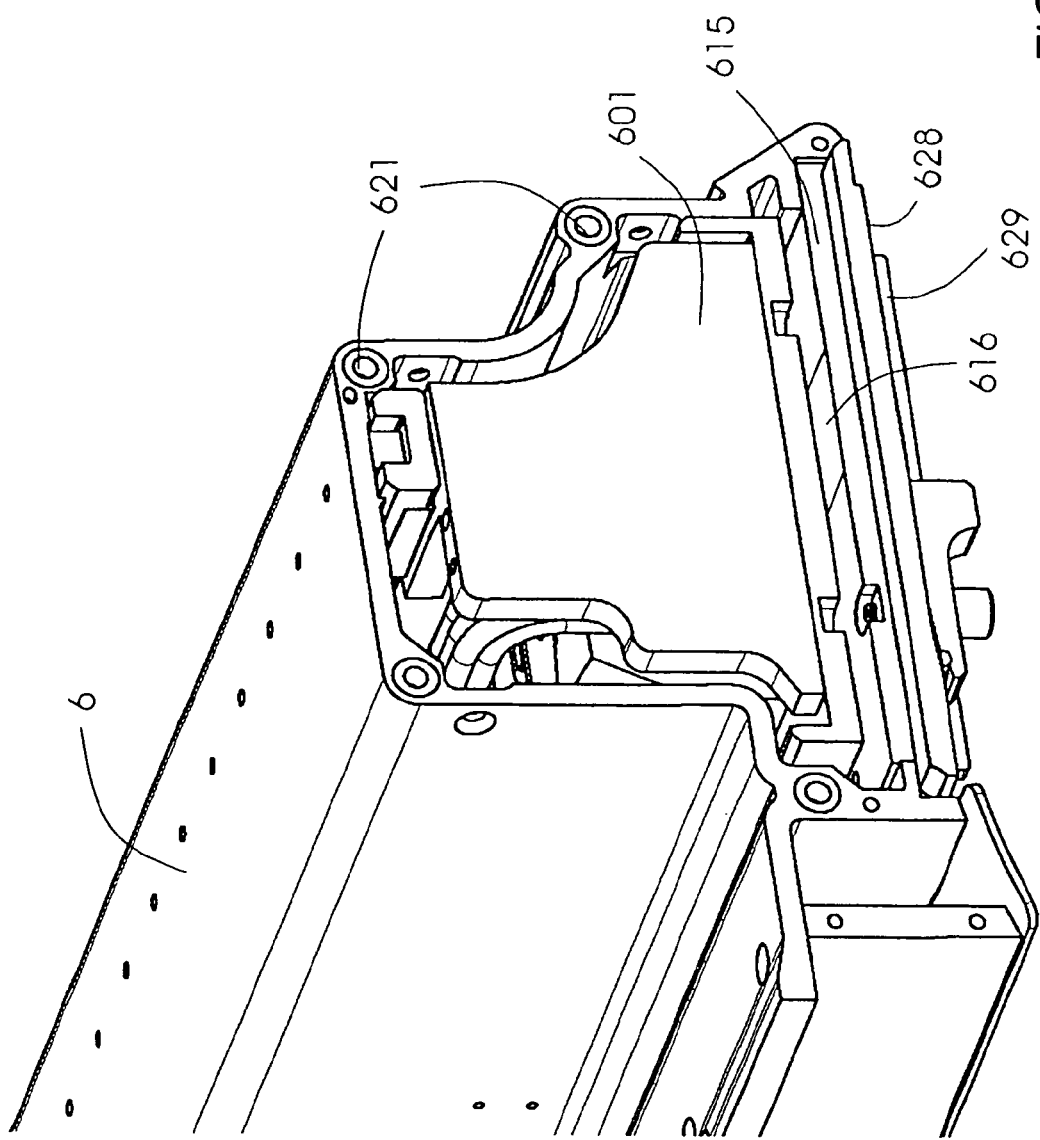
FIG. 4 is a further enlarged, perspective and cross-sectional view through the measuring beam of FIG. 3.

The side view of the measuring beam 6, shown in FIG. 4, shows, in addition to the substantially U-shaped profile of the measuring beam 6, the coolant ducts 621 running in the U profile, which are connected to the closed circuit at the two end faces of the measuring beam 6 by the coolant ducts 617 in the side walls 601. Furthermore, the glass cover 615 in the base of the measuring beam can be seen, which protects the sensitive measuring modules 603 on the measuring carriage 605 against contamination. The U-shaped housing of the measuring beam 6, the side walls 601 and the measuring beam base 615 with its glass inserts 616 are connected to one another by seals, so that no dust or liquids can get into the interior of the measuring beam 6. Furthermore, on the outside of the base 615 there is a dirt-repellant surface 628, over which there extend webs 629 located transversely with respect to the longitudinal extent of the measuring beam. The webs 629 hold the printing material 705 at a distance when it is being measured and, in this way, avoid direct contact between the printing material 705 and the base 615. The webs 629 can also be coated in a dirt-repellant manner.

Figure 5:
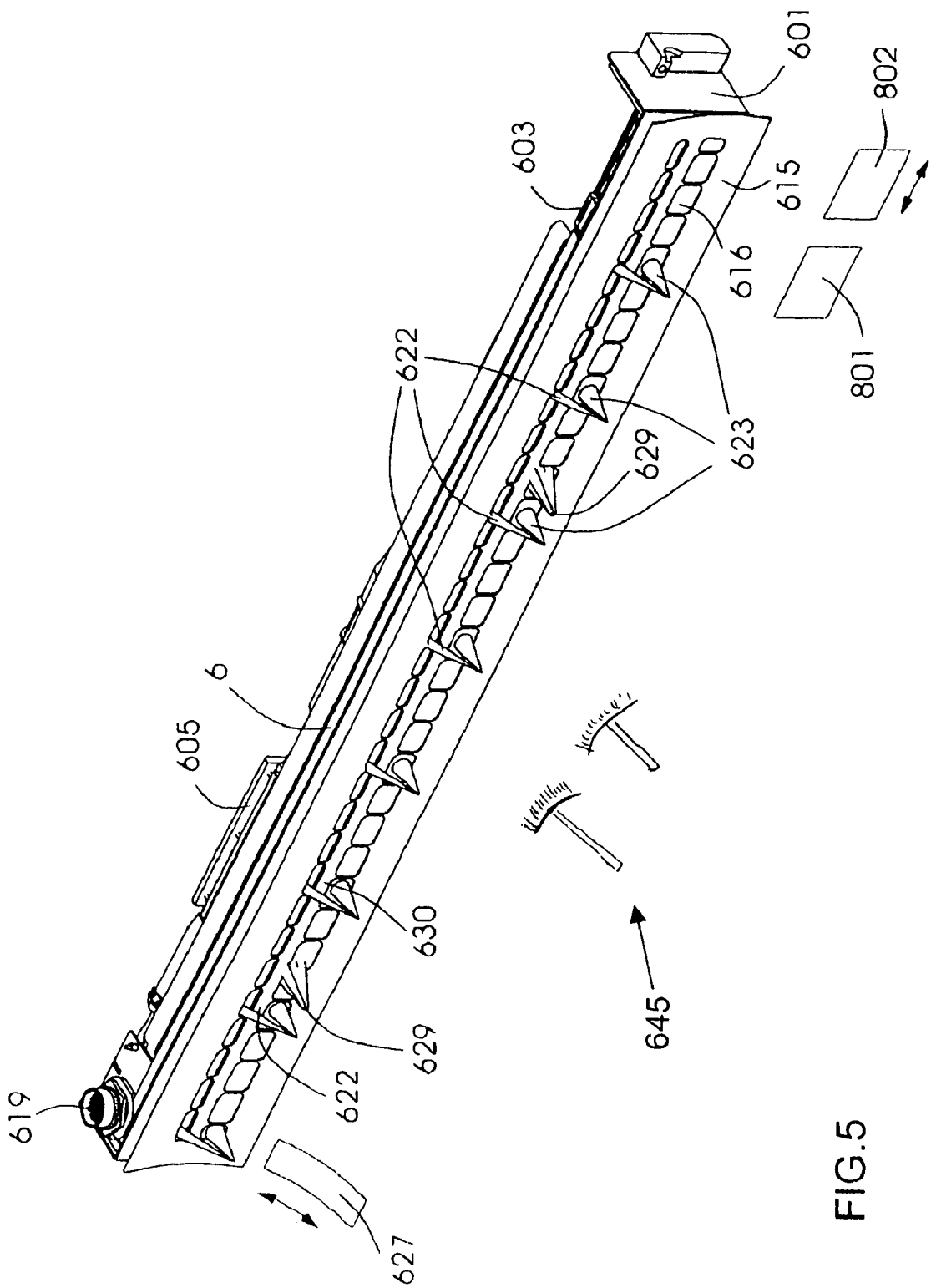
FIG. 5 is a bottom-perspective view of the measuring beam of FIG. 3.

FIG. 5 shows a view of the measuring beam 6 from below, in which it is possible to see the measuring beam base 615 well. The measuring carriage 605 has the eight measuring modules 603, each of which include the actual measuring heads 623 and illuminating modules 623. In order to be able to measure the entire width of a printed sheet having 32 inking zones, after each measuring operation the measuring carriage 605 is moved laterally by one or more measuring areas. The distance between the measuring modules 603 is thus four inking zones, so that the measuring modules 603 measure exactly each fourth inking zone in parallel. Following four sensing operations, the sheet has then been measured over all 32 inking zones of a color. If printing is carried out with four colors, 16 sensing operations are accordingly necessary. Furthermore, a movable shutter 627, which is able to cover a measuring module 603, can be seen in FIG. 5. The shutter 627 can be present on every module 603 and is driven electrically or mechanically, but a common shutter 627 for all of the modules 603 can also be used. In FIG. 5, the shutter 627 can be moved in the sheet transport direction, transversely with respect to the measuring beam 6, and protects the optics of the measuring modules 603 against damage between the measuring operations. It can also cover all of the underside of the measuring beam 6 between the individual measuring operations. For this purpose, the drive of the shutter 627 is coupled to the computer 200 of the printing press.

Disposed at one end 601 or else at both ends in FIG. 5, is a calibration surface 801, to which the outer measuring modules 603 can be moved. If a measuring module 603 is positioned above the calibration surface 801, then this standardized surface is measured. The surface is a white tile which corresponds to paper white. A measuring module 603 can be calibrated at any time between two measurements on the printing material 705 by measuring the tile 801. The measuring modules 603 which cannot move to the tile 801 are calibrated through the use of transfer calibration from the adjacent measuring modules 603. In order to protect the tile 801 against contamination, it can likewise be closed through the use of a cover 802 that can be moved laterally. Thus, the tile 801 is always kept covered by the cover 802 between the calibration measurements.

The webs 629 which are dirt-repellent and hold the sheet at a distance, can also be seen in FIG. 5. These webs 629 are connected to the cover 615 of the measuring beam 6. The measuring beam is sealed off by the glass layer 616 located under the cover 615. For the purpose of cleaning the glass layer 616, the cover 616 having the webs 629 and the cut-outs for the clear view of the measuring modules 603 can be folded away onto the sheet 705 or removed, so that all of the area of the glass layer 616 can easily be cleaned. Cleaning tools 645 are provided which are matched to the shape of the part of the sensing device 6 to be cleaned. These cleaning tools 645 are in particular matched to the shape of the areas to be cleaned, in order for example, to make the cleaning operation of the glass layer 616 easier in this way.

Figure 6:
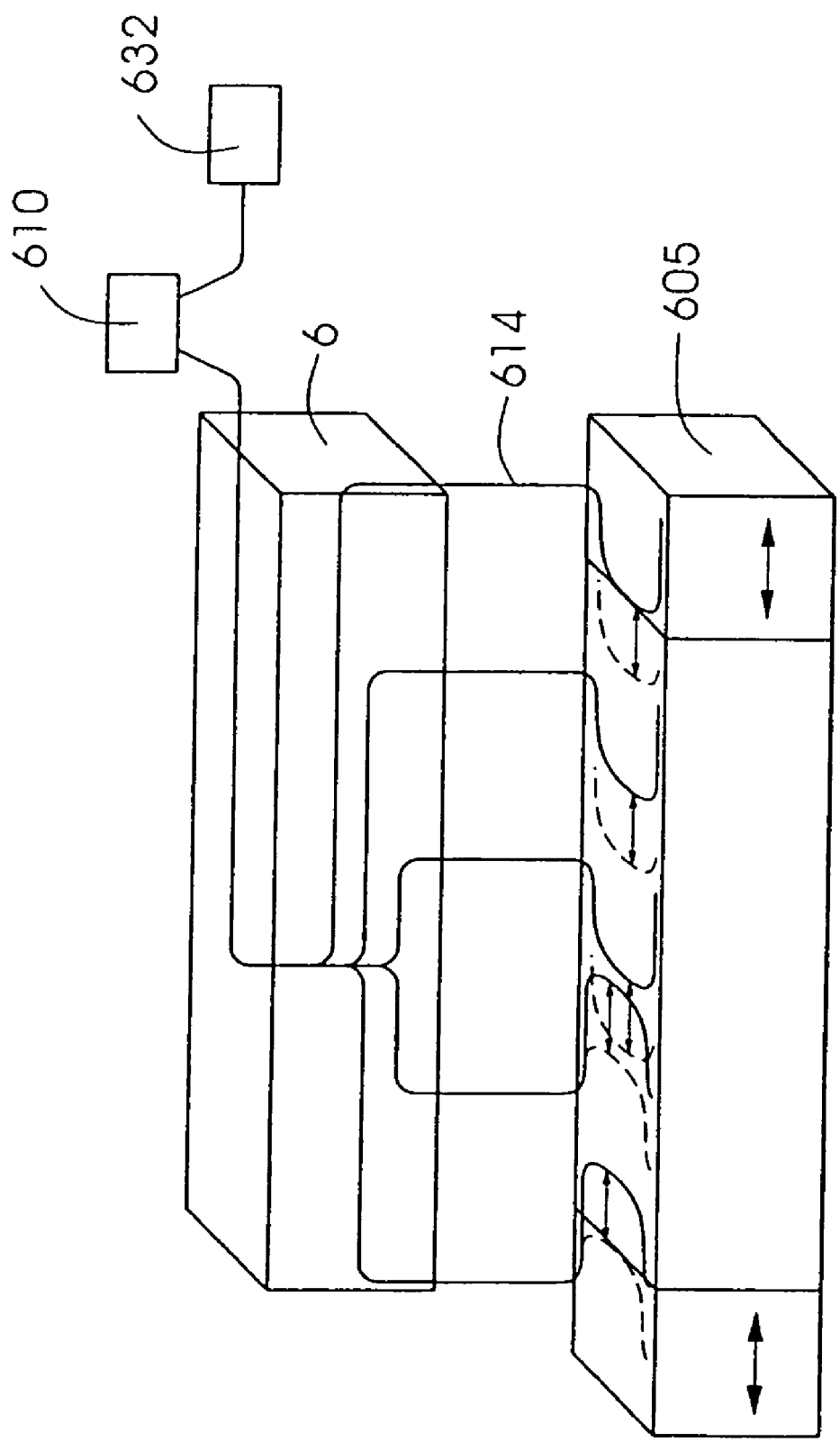
FIG. 6 is a further enlarged, perspective view of an optical waveguide configuration in the measuring beam.

In addition to the possibility, illustrated in FIG. 3, of having light sources 610 disposed on the measuring carriage 605, it is also possible, according to the configuration in FIG. 6, to fit the flash lamp 610 outside the measuring carriage 605 and even outside the measuring beam 6. In this case it is necessary to use flexible optical waveguides 614, which connect the non-moving parts of the measuring beam 6 and the measuring carriage 605. However, the flexible waveguides 614 can also be used when the lamp 610 is located on the carriage 605, as in FIG. 3. In this case, the optical waveguides 614 can be led separately to each measuring module 603, as in FIG. 6, but it is also possible to bundle the optical waveguides 614 at one point and to lead them to the respective measuring module 603 over longer paths in the interior of the measuring carriage 605. If all of the measuring modules 603 receive the light from a single light source 610, it is ensured that all of the measuring modules 603 use the same light during the measurement and therefore the measuring conditions for all of the modules 603 are the same. It is also possible for an additional optical waveguide 614 to be connected to the lamp 610 and to open on the other side in a light reference measuring head 632. This light reference measuring head 632 has the task of measuring the light from the lamp 610 and, in the event of a change, of outputting a signal relating to maintenance and inspection. Thus, a defective lamp 610 or one no longer equipped with sufficient illuminating power as a result of aging, can be detected in good time.

As an alternative to flexible optical waveguides 614 as in FIG. 6, the principle of the optical trombone can also be used, as is shown in FIGS. 7A and 7B. In this case, the optical waveguides of the measuring carriage 605 and of the measuring beam 6 in each case end at end faces 625, 626 of the same, so that they are always located and aligned accurately with respect to one another. Disposed between the end faces 626 of the optical waveguides of the measuring carriage 605 and the end faces 625 of the measuring beam 6, there is an optical interspace 624 which, as is shown in FIGS. 7A and 7B, has a different size depending on the position of the measuring carriage 605. The optical interspace 624 between the optical waveguides can be bridged by it being silvered. The light beams emerging from the optical waveguides of the measuring beam 6 can be coupled into the optical waveguides in any position of the measuring carriage 605, through the use of this silvering. Such an optical trombone is less susceptible to wear than flexible optical waveguides 614, which is of enormous importance in view of million-fold measuring operations. This is because it has transpired that flexible optical waveguides 614 tend to break after relatively few measuring operations and then have to be replaced.

Figure 8A:
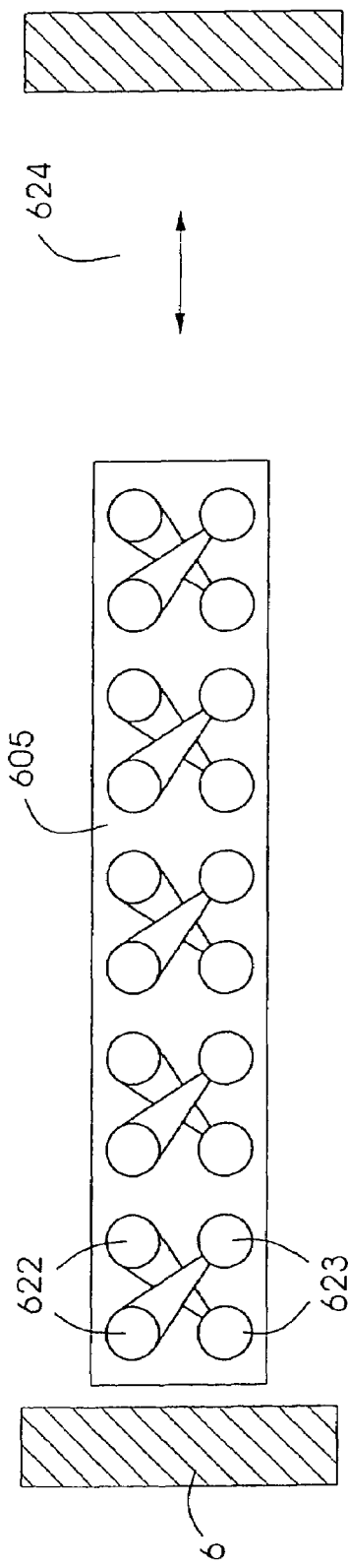
FIG. 8A is a partly-sectional view of a crossover configuration of measuring heads and illuminating devices.
Figure 8B:
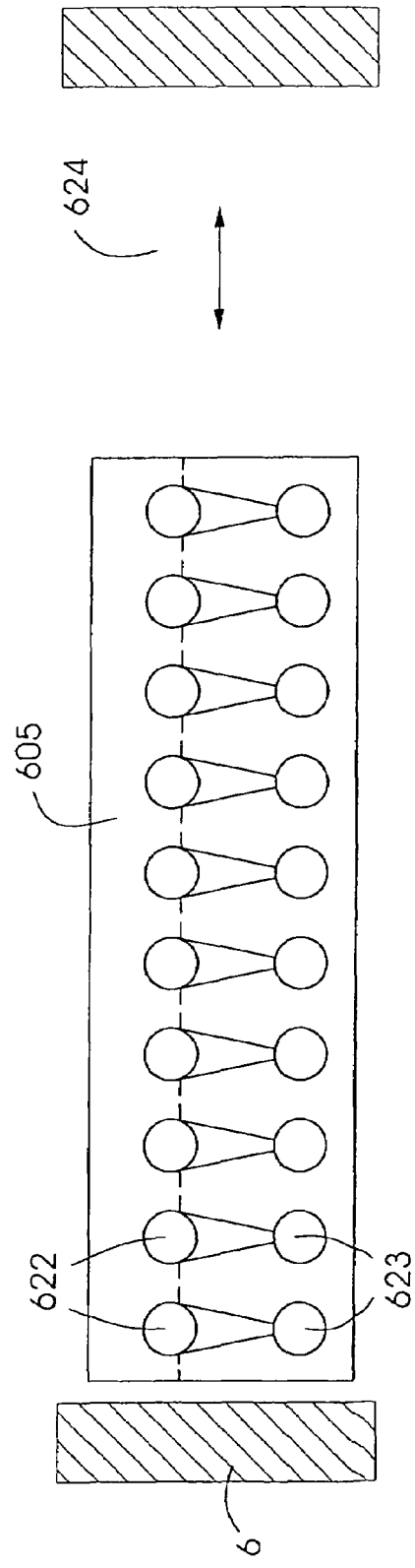
FIG. 8B is a partly-sectional view of a conventional configuration of measuring heads and illuminating devices in the measuring beam.

FIGS. 8A and 8B each show the measuring beam 6 seen from below, with two different configurations of measuring heads 622 and illuminating modules 623. In the configuration according to FIG. 8A, the measuring heads 622 and the illuminating modules 623 are aligned so as to cross over one another, so that the light which is reflected from the printing material is not sensed by the measuring head 622 located directly opposite, but is crossed over like a cross. Such a configuration permits the disposition of many measuring heads in a small space, since there the distance between the measuring heads 622 and the opposite illuminating modules 623 can be smaller as compared with a configuration according to FIG. 8B, in which the measuring heads 622 sense the reflected light from exactly opposite illuminating modules 623. The smaller space in FIG. 8A results from the diagonal crossing, since the distance between the illuminating modules 623 and the associated measuring heads 622 cannot be reduced arbitrarily. The distance is defined by the beam path from the illuminating modules 623 to the printing material and back to the measuring head 622. With the crossover construction, the width of the respective measuring beam 6 and measuring carriage 605 can be reduced. Since the space required is a decisive criterion, given the restricted space in the vicinity of the press nip 100 of a printing unit 4, 5, the configuration according to FIG. 8A is better suited to this case.

Figure 9:
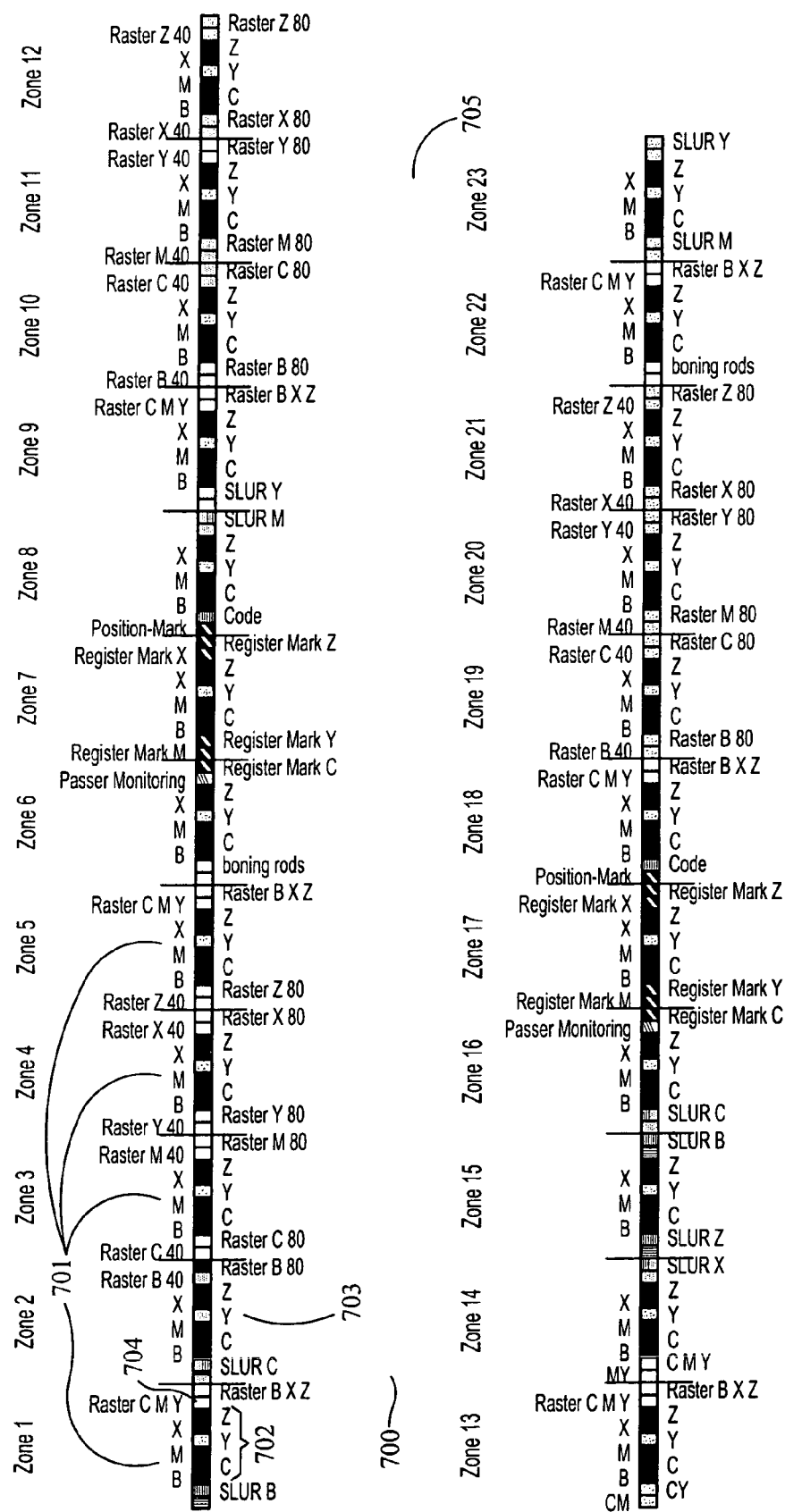
FIG. 9 is a plan view of a print control strip on a printing material.

A print control strip 700 on a printed sheet 705 is illustrated in FIG. 9. The print control strip 700 and the actual printed image are printed onto the sheet 705 in the printing units 4, 5 of the printing press 1. After the last printing unit 5, the sheet 705 and the print control strip 700 are complete and can be measured by the measuring beam 6. The sheet 705 in this case is present in what is known as the medium format, that is to say with a sheet width of 74 cm, and has 23 inking zones 701, 703. Each inking zone 701, 703 includes 6 color measuring areas 702 and four further measuring areas 704. These inking zones 701, 703 are measured by the measuring modules 603 of the measuring beam 6. Normally, only one of the measuring areas 702, 704 per color separation and inking zone 701, 703 on a sheet 705 is measured by a measuring module 603. In the case of 23 inking zones 701, 703, six measuring modules 603 and 10 measuring areas 702, 704 per inking zone, this results in 40 measuring operations on 40 printed sheets 705 before all of the measuring areas 701, 703 have been registered once. More measuring modules 603 have to be provided for more measurements on fewer sheets. Furthermore, a plurality of print control strips 700 can also be applied to a sheet, for example one at the sheet start and one at the center of the sheet or the end of the sheet. Alternatively, during continuous printing operation, that is to say when the printing press 1 is running at production speed and all of the measuring areas 702, 704 have reached their desired state, the measuring modules 603 can also be placed over specific measuring areas.702, 704 which contain color information about a plurality or all of the colors. The measuring modules 603 then even do not have to be moved at all or much more rarely, since the color information is present in locally compact form in one measuring area. In the event of changes within the specific measuring areas, then the measuring mode is changed again, and all of the measuring areas 702, 704 are measured again as in the start-up phase.

Figure 10:
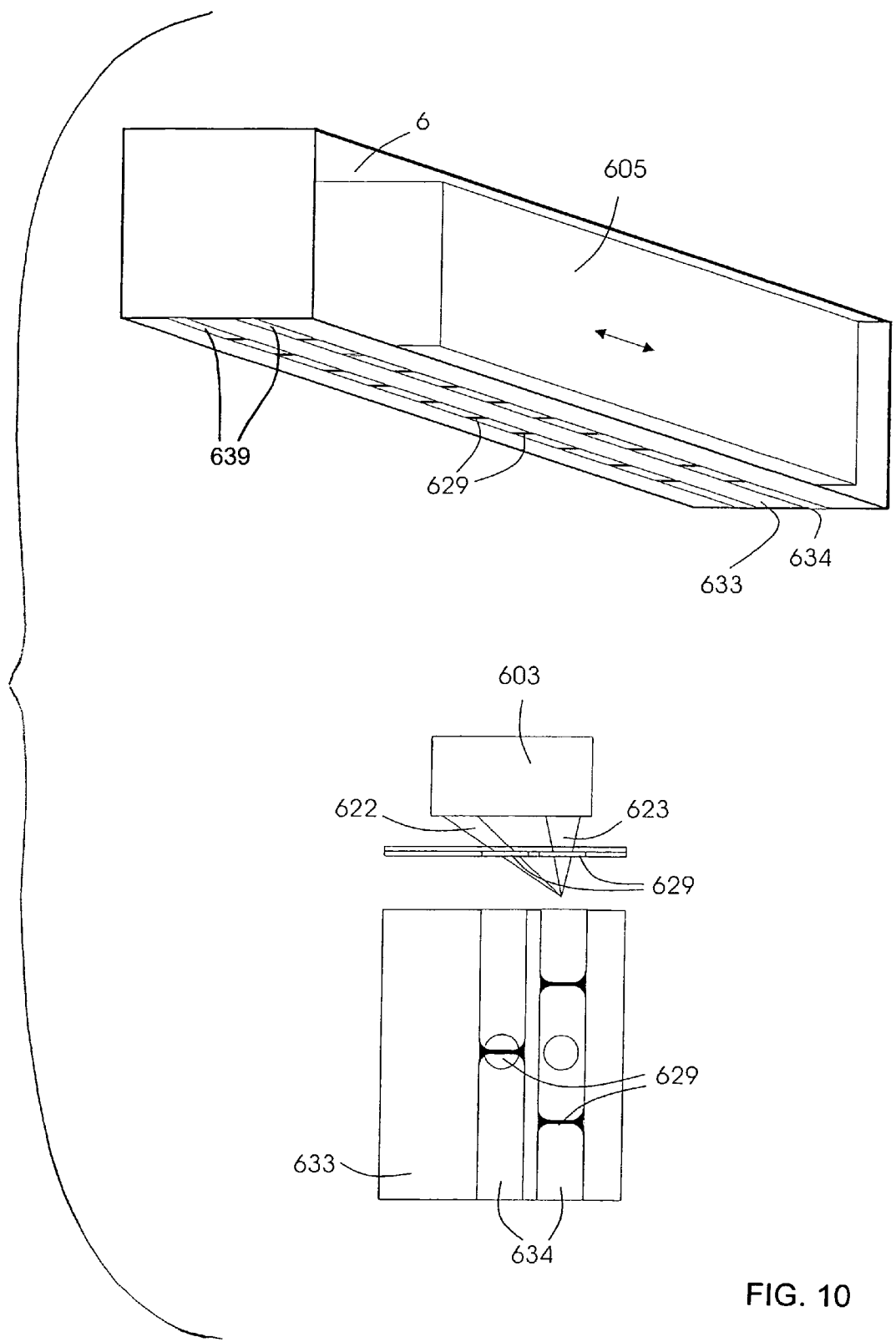
FIG. 10 is a perspective view of a measuring beam having a glass base and a cover formed as a slotted sheet guide.

FIG. 10 shows an embodiment similar to that of FIG. 5. In both embodiments, a measuring carriage 605 that can be moved laterally is located in an encapsulated, sealed measuring beam 6. However, in FIG. 10, the measuring beam has a continuous glass cover 634 which closes the underside of the measuring beam 6. There is also a sheet guide plate 633 on the outside of the measuring beam 6, over the continuous glass cover 634, for sheet guidance, which has two slots 639 in the longitudinal direction. The measuring modules 603 including the measuring head 622 and the illuminating module 623 in the measuring carriage 605 are able to measure a printing material 705 running through under the sheet guide 633 through these slots 639 and the glass cover 634. In addition, there are webs 629 disposed on the outside of the glass cover 634 and within the slots 639. The webs 629 prevent the printing material 705 from touching the glass cover 634 and therefore soiling the latter. Since the webs 629 provided as in FIG. 10 can be in the beam path of the measuring module 603 under certain circumstances, because the measuring carriage 605 must measure over the entire width of the printing material, a compensation device is provided which compensates for the influence of the webs 629 in the beam path of the measuring modules 603. Such a compensation device has already been described previously in this application.

Figure 11:
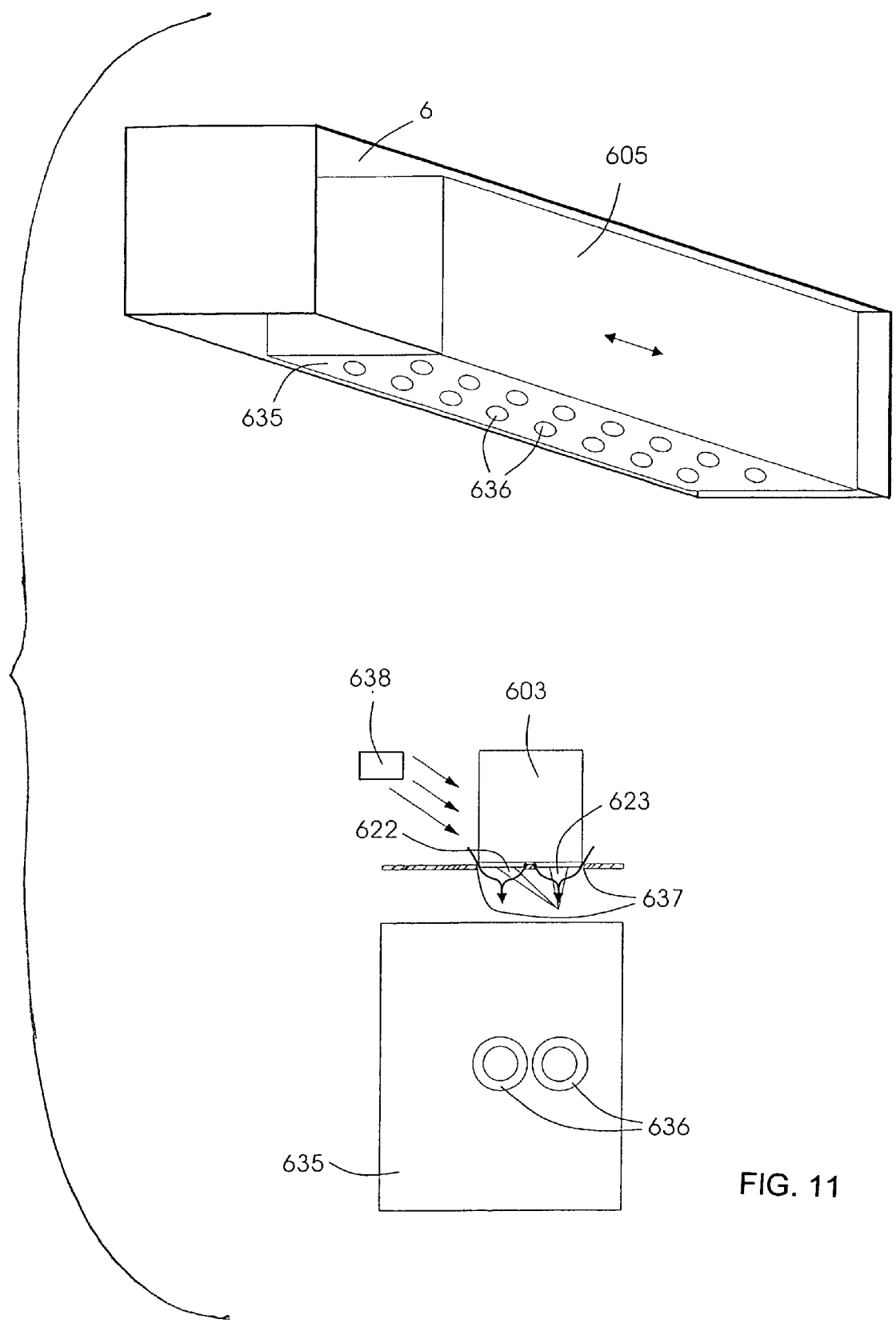
FIG. 11 is a perspective view of an open measuring beam having a sealed measuring carriage.

An alternative embodiment to FIG. 10 is shown in FIG. 11. In this case too, a measuring carriage 605 that can be moved is located in a measuring beam 6, but the measuring beam is open at the bottom, for which reason the measuring carriage 605 is closed by a base 635. For this purpose, the measuring carriage 605 has a base 635 made of sheet metal, which is additionally provided with glass viewing openings 636. The glass openings 636 are positioned exactly under the beam paths of the measuring modules 603. Therefore, in FIG. 11 with 8 measuring modules 603 on the measuring carriage 605, exactly 16 glass viewing openings 636 are provided underneath the 8 measuring heads 622 and 8 illuminating modules 623. The glass openings 636 can be circular, as in FIG. 11, but can also be oval, rectangular or configured in another shape. In addition to the glass viewing openings 636, there are also small blown air ducts 637 in the base 635 of the measuring carriage, through which blown air can escape from the interior of the measuring carriage 605. This blown air is used for the purpose of keeping the printing material 705 at a distance from the base 635, in order to avoid contact with the sheet 705 and therefore contamination of the glass openings 636. At the same time, foreign bodies are prevented from penetrating into the interior of the measuring carriage 605 from outside, through the use of the positive pressure produced in the interior of the measuring carriage 605 by the blown air. Blown air is applied to the blown air ducts 637 through the use of a blown air source 638, for example a small compressor or fan in the interior of the measuring carriage 605.

Figure 12D:
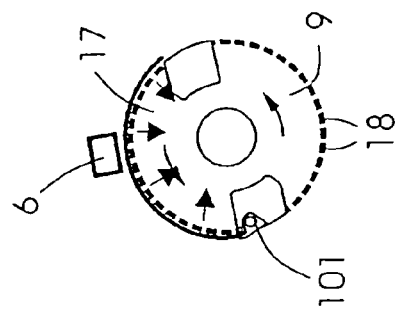
FIG. 12D is a side-elevational view showing sheets held by vacuum during the measuring operation.
Figure 12C:
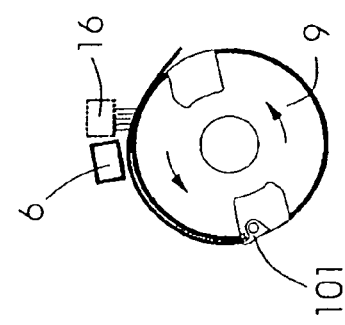
FIG. 12C is a side-elevational view showing sheets held by grippers and a blowing device during the measuring operation.
Figure 12B:
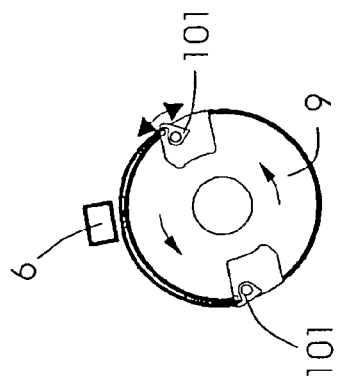
FIG. 12B is a side-elevational view showing sheets held by two grippers during the measuring operation.
Figure 12A:
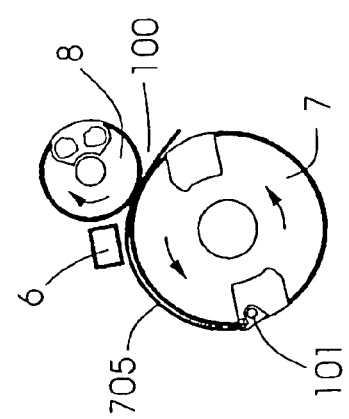
FIG. 12A is a side-elevational view showing sheets held by grippers and a press nip during a measuring operation.

FIGS. 12A, 12B, 12C and 12D show various possible ways of fixing the printing material 705 during the measuring operation by the measuring beam 6 in a sheet-fed rotary printing press 1. In addition to the possibility known from FIG. 1 and shown in FIG. 12A, of fixing the printing material 705 at its one end through the use of a sheet transport gripper 101 and at its other end by the press nip 100 between the impression cylinder 7 and the blanket cylinder 8, there are further possible ways of fixing the sheet 705, even when it is not in the press nip 100. According to FIG. 12B, a sheet 705 is held at both ends by transport grippers 101 on a transport cylinder 9 and in this way is fixed under the measuring beam 6 during the measurement. In FIG. 12C, instead of at least the transport gripper 101 trailing in the sheet transport direction, a blowing device 16 can also be installed above the transport cylinder 9, which presses the free end of the sheet 705 not fixed in a gripper onto the transport cylinder 9 and thus fixes it. Furthermore, a construction according to FIG. 12D can also be employed. In this configuration, the sheet 705 is fixed on the transport cylinder 9 substantially through the use of vacuum. To this end, the cylinder 9 has a plurality of air openings 18 on the cylinder surface which comes into contact with the sheet 705. The air openings 18 are connected to a vacuum chamber 17 in the interior of the cylinder 9. The vacuum fixes the sheet 705 on the cylinder in this way, which can additionally be assisted by a transport gripper 101, but does not have to be so assisted. The vacuum chamber 17 can be a constituent part of a suction pump in the interior of the cylinder 9 or can be connected to a suction pump outside the cylinder 9.

Figure 13:
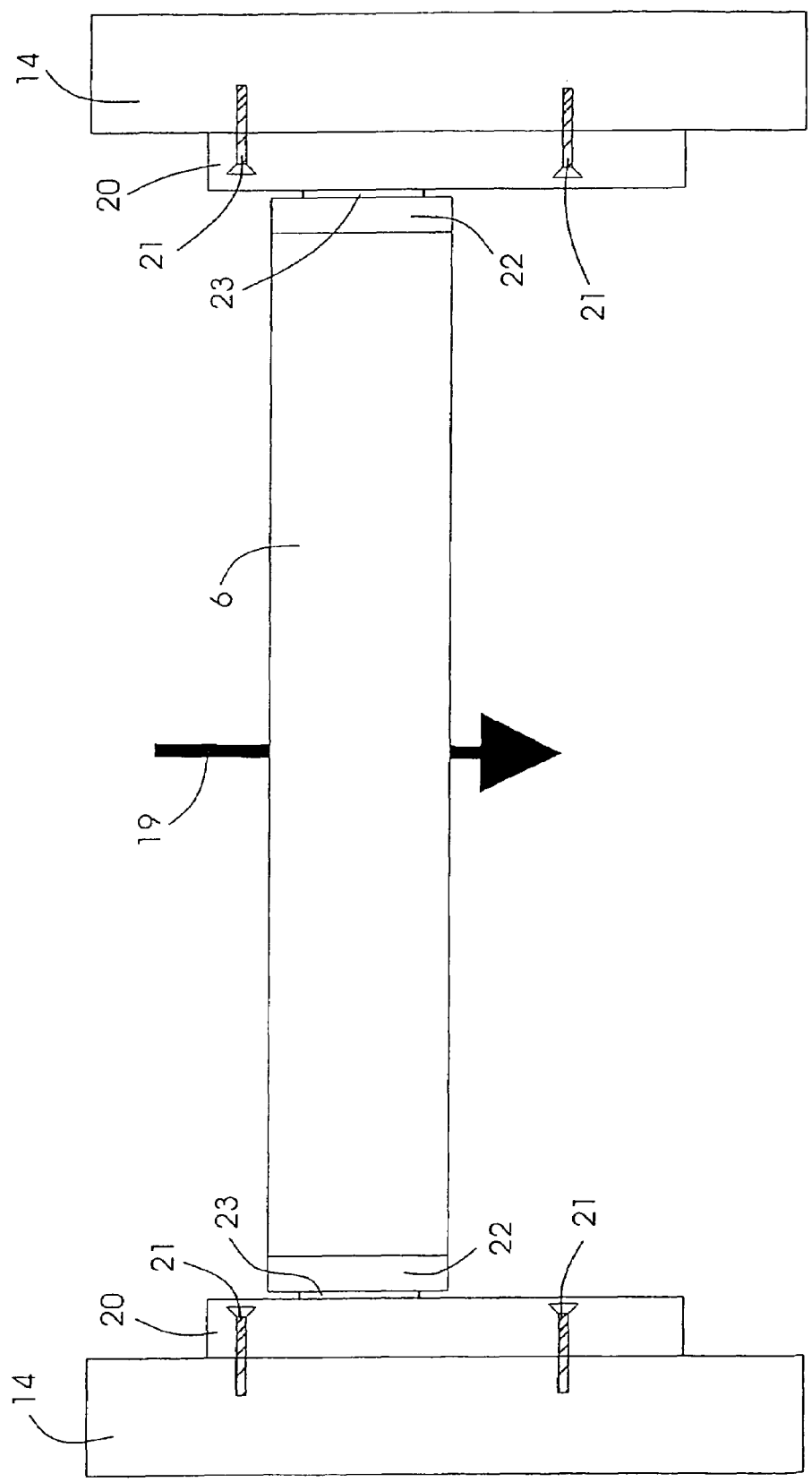
FIG. 13 is a plan view of the fixing of the measuring beam in the printing unit of a printing press.

FIG. 13 illustrates how the measuring beam 6 is mounted in a printing unit of a printing press 1. In the plan view of the installation location in the printing press 1, it can be seen that the measuring beam 6 is in principle installed transversely with respect to the sheet transport direction 19, between the side walls 14 of the printing press 1. Since the intention is that the measuring beam 6 can also be retrofitted in already existing machines, the mounting is made by two lateral mounting plates 20, which can in principle be installed in any printing press 1 as long as there is the necessary space. The mounting plates 20 can also compensate for different distances between the side walls 14, by being constructed to be of different thicknesses. The mounting plates 20 are fixed to the side walls 14 through the use of mounting screws 21 and carry the mounting for the measuring beam 6. The measuring beam 6 has covers 22 at each of its ends, which enclose the measuring beam 6 and carry bearings 23. These bearings 23 support the measuring beam 6 with respect to the mounting plates 20 and reduce vibrations which the printing press 1 would transmit to the measuring beam 6. The covers 22 can be configured in such a way that the measuring beam 6 can be removed simply from the covers 22.

We claim:

1. A printing press for processing sheet printing materials, the printing press comprising:
    at least one printing unit;
    a computer;
    a measuring device for monitoring printing quality during a printing process, said measuring device having a sensing device for measuring by color or spectrally to register the printing material, said sensing device being a measuring beam having a U-shaped profile with an interior, said U-shaped profile being open towards the printing material, and at least one movable measuring carriage being accommodated in said interior of said U-shaped profile; and
    at least one sheet-guiding element for leading the sheet printing material past said sensing device.

2. The printing press according to claim 1, wherein said sheet-guiding element is a sheet transport gripper.

3. The printing press according to claim 1, wherein said sheet-guiding element is a nip between two cylinders.

4. The printing press according to claim 1, wherein said sheet-guiding element is a transport cylinder.

5. The printing press according to claim 1, wherein the printing material is guided by at least one of blown air or vacuum.

6. The printing press according to claim 1, wherein said at least one printing unit has a side outputting the printing material and a press nip, and said sensing device is fitted in said side of said at least one printing unit close to said press nip.

7. The printing press according to claim 1, wherein said at least one sheet-guiding element includes a transport gripper of a sheet guiding drum and a press nip of said at least one printing unit, holding the printing material in said at least one printing unit during a sensing operation.

8. The printing press according to claim 1, wherein said sensing device additionally measures densitometrically.

9. The printing press according to claim 1, which further comprises a compensation device connected to said computer to compensate for an influence of light falling on the printing material.

10. The printing press according to claim 1, wherein said sensing device is for carrying out register measurement, position detection of register marks and determination of a type of printing material.

11. The printing press according to claim 1, wherein said at least one printing unit includes a last printing unit as seen in a printing material transport direction, and said sensing device is incorporated in or after said last printing unit.

12. The printing press according to claim 1, which further comprises a sheet turning device, said sensing device being one of a plurality of sensing devices including at least one sensing device disposed before said sheet turning device and a sensing device disposed after said sheet turning device, as seen in a printing material transport direction.

13. The printing press according to claim 1, wherein said measuring beam is mounted for displacement in its longitudinal direction.

14. The printing press according to claim 1, wherein said sensing device is mounted for rotation, pulling out or replacement.

15. The printing press according to claim 1, wherein said measuring beam has at least one removable side wall.

16. The printing press according to claim 1, wherein said measuring carriage has at least one measuring module.

17. The printing press according to claim 16, which further comprises electronics disposed outside said measuring beam for processing signals from said measuring modules.

18. The printing press according to claim 16, which further comprises electronics, disposed inside said measuring beam or said measuring modules, for processing signals from said measuring modules.

19. The printing press according to claim 16, wherein said at least one measuring module is provided with at least one moving mechanical shutter.

20. The printing press according to claim 19, which further comprises at least one drive for driving said mechanical shutter as a function of an operating state of the printing press.

21. The printing press according to claim 1, wherein said measuring carriage has at least one register sensor.

22. The printing press according to claim 1, wherein said sensing device has at least one illuminating device.

23. The printing press according to claim 1, which further comprises a motor driving said measuring carriage for movement in said U-shaped profile.

24. The printing press according to claim 1, wherein said sensing device is configured as a sheet-guiding element for a sheet-fed rotary printing press.

25. The printing press according to claim 1, wherein said sensing device is for detecting a position of a print control strip and registering a measuring time for a color measurement.

26. The printing press according to claim 1, wherein said sensing device is connected to said computer.

27. The device according to claim 26, wherein said sensing device has at least one measuring module and calibration data for each measuring module is to be stored in said computer.

28. The device according to claim 1, wherein said sensing device has an Ethernet interface or another standardized computer interface.

29. The printing press according to claim 1, wherein said sensing device has at least one measuring module and at least one illuminating device with optical waveguides and at least one light source, said optical waveguides having one end assigned to individual measuring modules and another end assigned to said at least one light source in a thoroughly mixed bundle.

30. The printing press according to claim 29, wherein said at least one light source is disposed outside said measuring beam.

31. The printing press according to claim 1, wherein said sensing device has at least one temperature sensor.

32. The printing press according to claim 1, wherein said sensing device has a cooling device.

33. The printing press according to claim 1, which further comprises a transparent cover protecting said sensing device against contamination.

34. The printing press according to claim 33, wherein said transparent cover is formed of toughened glass.

35. The printing press according to claim 33, wherein said transparent cover is replaceable.

36. The printing press according to claim 1, wherein said sensing device has a sealed housing.

37. The printing press according to claim 1, wherein said sensing device has at least one part with dirt-repellent surfaces.

38. The printing press according to claim 1, wherein said sensing device is to be shielded against penetration of foreign bodies by air flowing out of said sensing device.

39. A printing press for processing sheet printing materials, the printing press comprising:
at least one printing unit;
a computer;
a measuring device for monitoring printing quality during a printing process, said measuring device having a sensing device for measuring by color or spectrally to register the printing material, said sensing device having at least one illuminating device, said at least one illuminating device providing illumination for being synchronized with a measuring time of said sensing device; and
at least one sheet-guiding element for leading the sheet printing material past said sensing device.

40. A printing press for processing sheet printing materials, the printing press comprising:
at least one printing unit;
a computer;
a measuring device for monitoring printing quality during a printing process, said measuring device having a sensing device for measuring by color or spectrally to register the printing material, said sensing device having at least one measuring module and at least one illuminating device with optical waveguides and at least one light source, said optical waveguides having one end assigned to individual measuring modules and another end assigned to said at least one light source in a thoroughly mixed bundle, said sensing device being a measuring beam having a U-shaped profile with an interior, said U-shaped profile being open towards the printing material, at least one movable measuring carriage being accommodated in said interior of said U-shaped profile, and said at least one light source being disposed outside said measuring carriage; and
at least one sheet-guiding element for leading the sheet printing material past said sensing device.

41. The printing press according to claim 40, wherein said optical waveguides include a first bundle of optical waveguides disposed and aligned parallel to one another on said movable measuring carriage and having end faces and a second bundle of optical waveguides disposed on said measuring beam and having corresponding end faces, and said first and second bundles of optical waveguides define an interspace therebetween to be bridged by optics.

42. A printing press for processing sheet printing materials, the printing press comprising:
at least one printing unit;
a computer;
a measuring device for monitoring printing quality during a printing process, said measuring device having a sensing device for measuring by color or spectrally to register the printing material, said sensing device having at least one measuring module and at least one illuminating device with optical waveguides and at least one light source, said optical waveguides having one end assigned to individual measuring modules and another end assigned to said at least one light source in a thoroughly mixed bundle, said sensing device being a measuring beam having a U-shaped profile with an interior, said U-shaped profile being open towards the printing material, at least one movable measuring carriage being accommodated in said interior of said U-shaped profile, and said at least one light source being disposed in said measuring carriage; and
at least one sheet-guiding element for leading the sheet printing material past said sensing device.

43. A printing press for processing sheet printing materials, the printing press comprising:
at least one printing unit;
a computer;
a measuring device for monitoring printing quality during a printing process, said measuring device having a sensing device for measuring by color or spectrally to register the printing material;
a transparent cover protecting said sensing device against contamination, said sensing device containing a device for monitoring a condition of said transparent cover; and
at least one sheet-guiding element for leading the sheet printing material past said sensing device.

44. A printing press for processing sheet printing materials, the printing press comprising:
at least one printing unit;
a computer;
a measuring device for monitoring printing quality during a printing process, said measuring device having a sensing device for measuring by color or spectrally to register the printing material;

cleaning tools matched to a shape of parts of said sensing device to be cleaned; and at least one sheet-guiding element for leading the sheet printing material past said sensing device.

45. A printing press for processing sheet printing materials, the printing press comprising:

at least one printing unit;

a computer;

a measuring device for monitoring printing quality during a printing process, said measuring device having a sensing device for measuring by color or spectrally to register the printing material;

a transparent cover protecting said sensing device against contamination;

webs disposed on a side of said transparent cover of said sensing device facing the printing material; and at least one sheet-guiding element for leading the sheet printing material past said sensing device.

46. The printing press according to claim 45, wherein said webs are configured to be folded away against said cover or removed.

* * * * *